(12) United States Patent
Takenaka et al.

(10) Patent No.: US 10,188,577 B2
(45) Date of Patent: *Jan. 29, 2019

(54) ELASTIC FORCE GENERATING DEVICE

(71) Applicant: HONDA MOTOR CO., LTD., Minato-Ku, Tokyo (JP)

(72) Inventors: Toru Takenaka, Saitama (JP); Hiroshi Gomi, Saitama (JP); Yosuke Ikedo, Saitama (JP); Yoshinao Sodeyama, Saitama (JP); Kenichi Katagiri, Saitama (JP)

(73) Assignee: Honda Motor Co., Ltd., Tokyo (JP)

( * ) Notice: Subject to any disclaimer, the term of this patent is extended or adjusted under 35 U.S.C. 154(b) by 503 days.

This patent is subject to a terminal disclaimer.

(21) Appl. No.: 14/979,868

(22) Filed: Dec. 28, 2015

(65) Prior Publication Data

US 2016/0184166 A1 Jun. 30, 2016

(30) Foreign Application Priority Data

Dec. 26, 2014 (JP) .................................. 2014-266595

(51) Int. Cl.
*A61H 3/00* (2006.01)
*A61H 1/02* (2006.01)
*A61F 2/60* (2006.01)

(52) U.S. Cl.
CPC ................. *A61H 3/00* (2013.01); *A61F 2/60* (2013.01); *A61H 1/024* (2013.01); *A61H 1/0244* (2013.01); *A61H 1/0277* (2013.01); *A61H 1/0281* (2013.01); *A61H 2201/1207* (2013.01); *A61H 2201/1481* (2013.01);

(Continued)

(58) Field of Classification Search
CPC .. A61H 3/00; A61H 1/024; A61H 2201/5069; A61H 2201/5066; A61H 2201/164; A61H 2201/1635; A61H 2201/1614; A61H 2201/1481; A61H 2201/1207; A61H 1/0281; A61H 1/0277; A61H 1/0244; A61F 2/60

See application file for complete search history.

(56) References Cited

U.S. PATENT DOCUMENTS

2008/0289670 A1* 11/2008 Ashihara ................ B25J 9/0006
  135/65
2009/0292369 A1* 11/2009 Kazerooni ............. B25J 9/0006
  623/27

(Continued)

FOREIGN PATENT DOCUMENTS

JP   2012-100983 A   5/2012
JP   2014-508010 A   4/2014
WO   2012/125765 A2  9/2012

*Primary Examiner* — Quang D Thanh
(74) *Attorney, Agent, or Firm* — Carrier Blackman & Associates, P.C.; Joseph P. Carrier; Jeffrey T. Gedeon

(57) ABSTRACT

A joint power generating device (8) has a multilayer structure constituted by alternately stacking an elastic member (41), which incorporates a hermetically sealed air chamber, and a partition plate (42) with high stiffness, an elastic structure (31), which has a through hole (43) formed therein, and a flexible lengthy member (32) inserted in the through hole (43). The joint power generating device (8) is configured to transmit a force between the lengthy member (32) and the elastic structure (31) such that the force for compressing the elastic structure (31) increases as the tension on the lengthy member (32) increases.

15 Claims, 19 Drawing Sheets

(52) U.S. Cl.
CPC .. *A61H 2201/164* (2013.01); *A61H 2201/165* (2013.01); *A61H 2201/1614* (2013.01); *A61H 2201/1628* (2013.01); *A61H 2201/1635* (2013.01); *A61H 2201/5066* (2013.01); *A61H 2201/5069* (2013.01)

(56) References Cited

U.S. PATENT DOCUMENTS

| | | | | |
|---|---|---|---|---|
| 2009/0312844 | A1* | 12/2009 | Ikeuchi | A61H 3/008 623/40 |
| 2010/0152630 | A1* | 6/2010 | Matsuoka | A61H 3/008 601/35 |
| 2015/0051527 | A1* | 2/2015 | Potter | A61F 5/0125 602/16 |

* cited by examiner

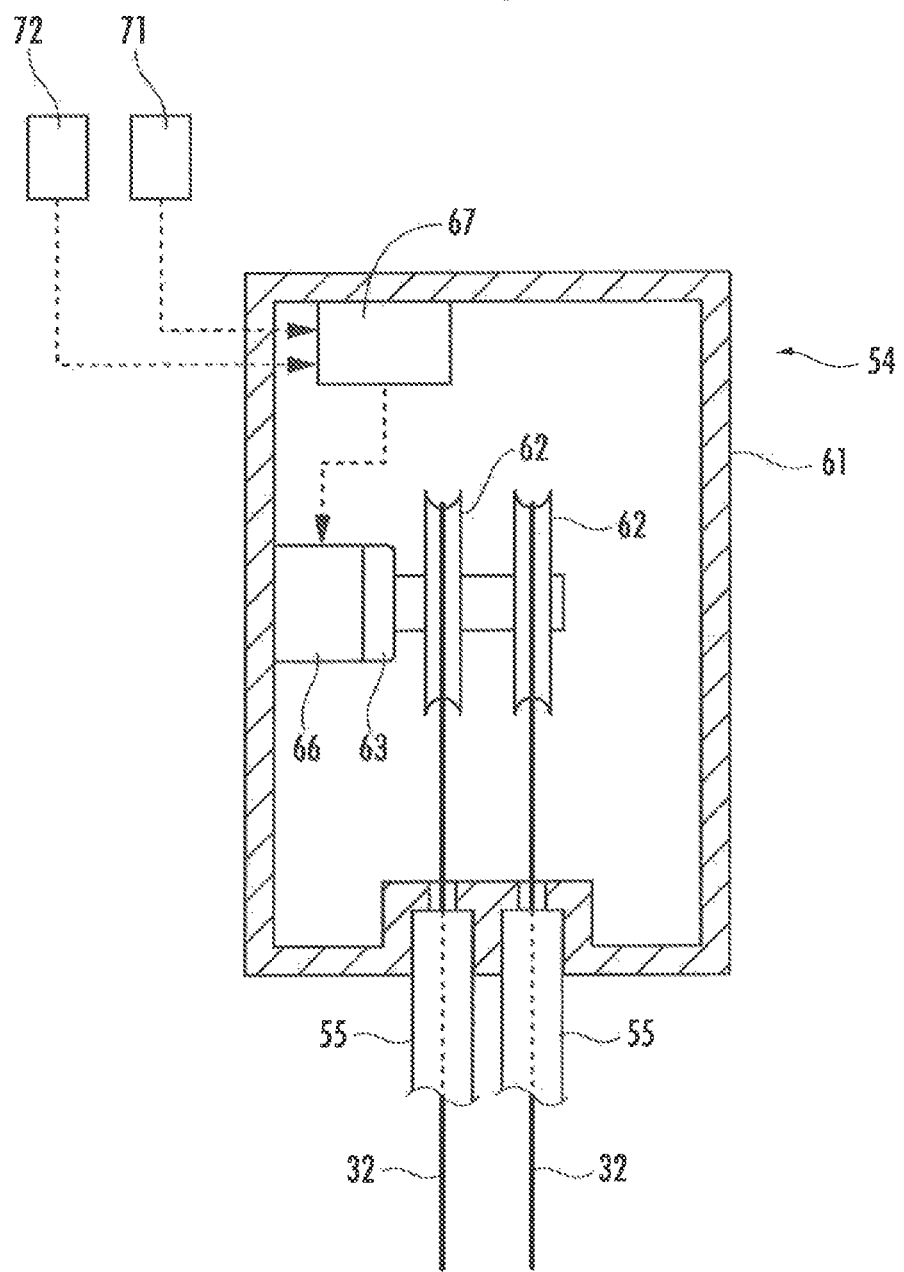

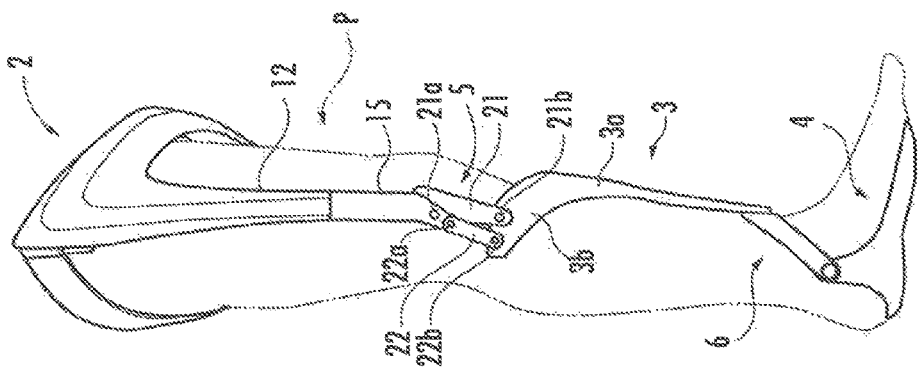
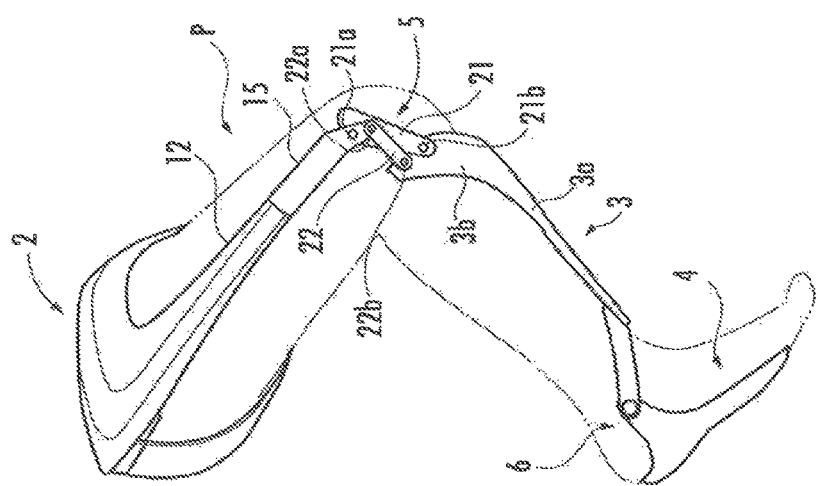
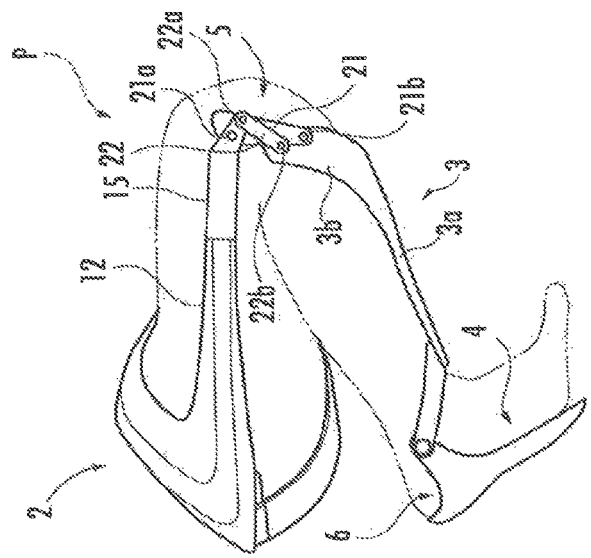

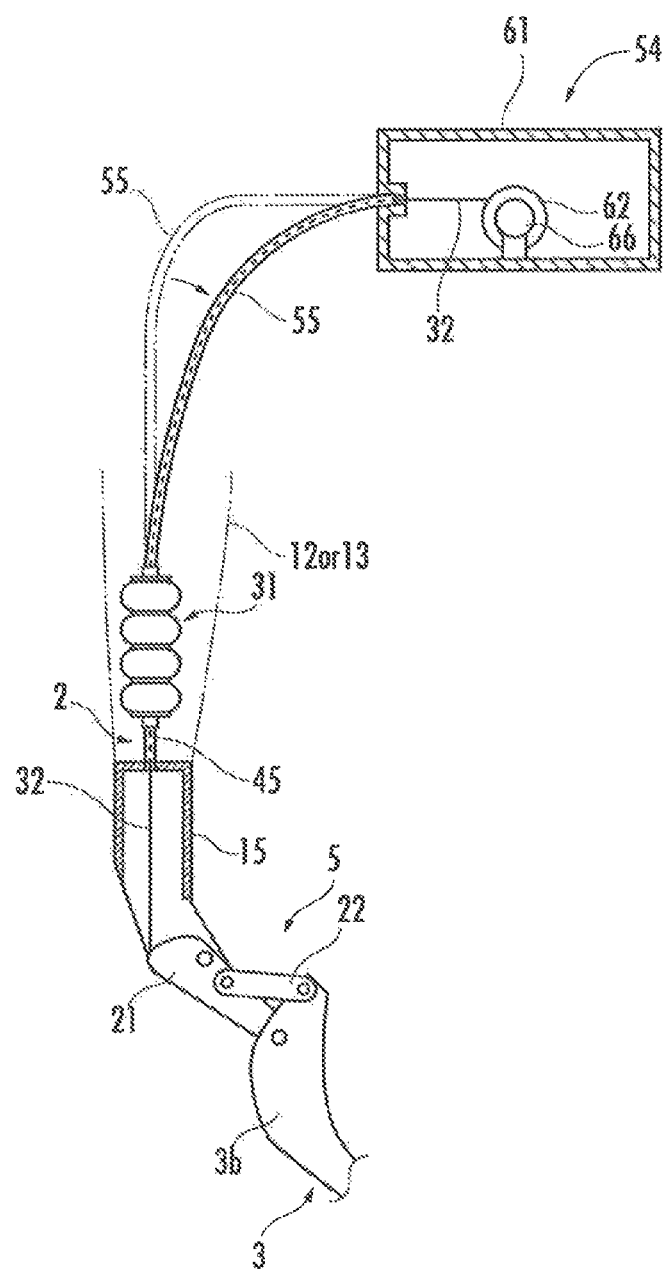

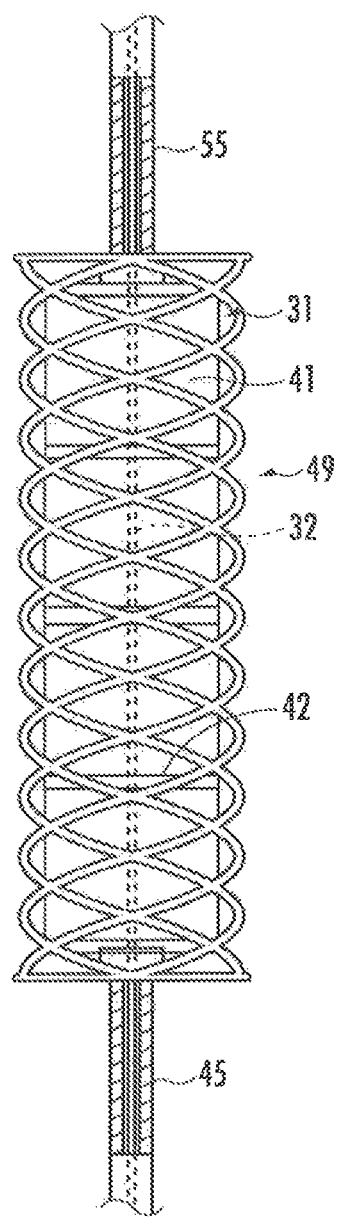

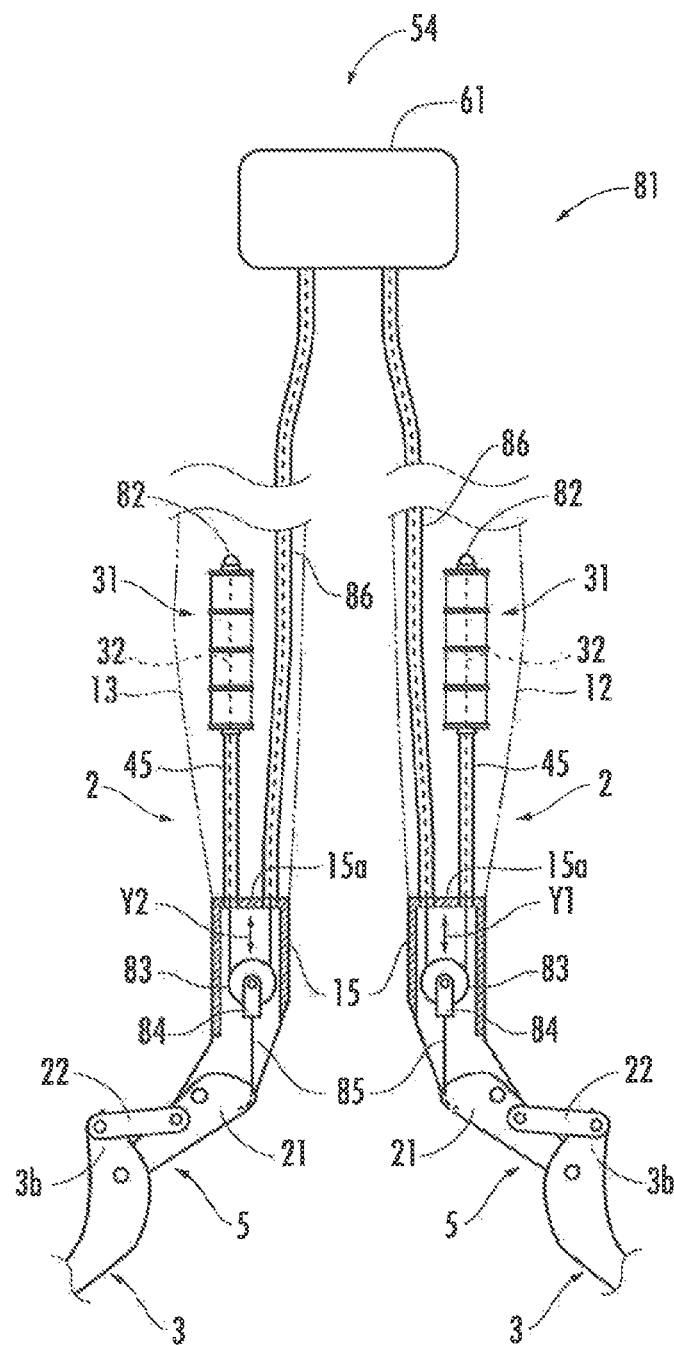

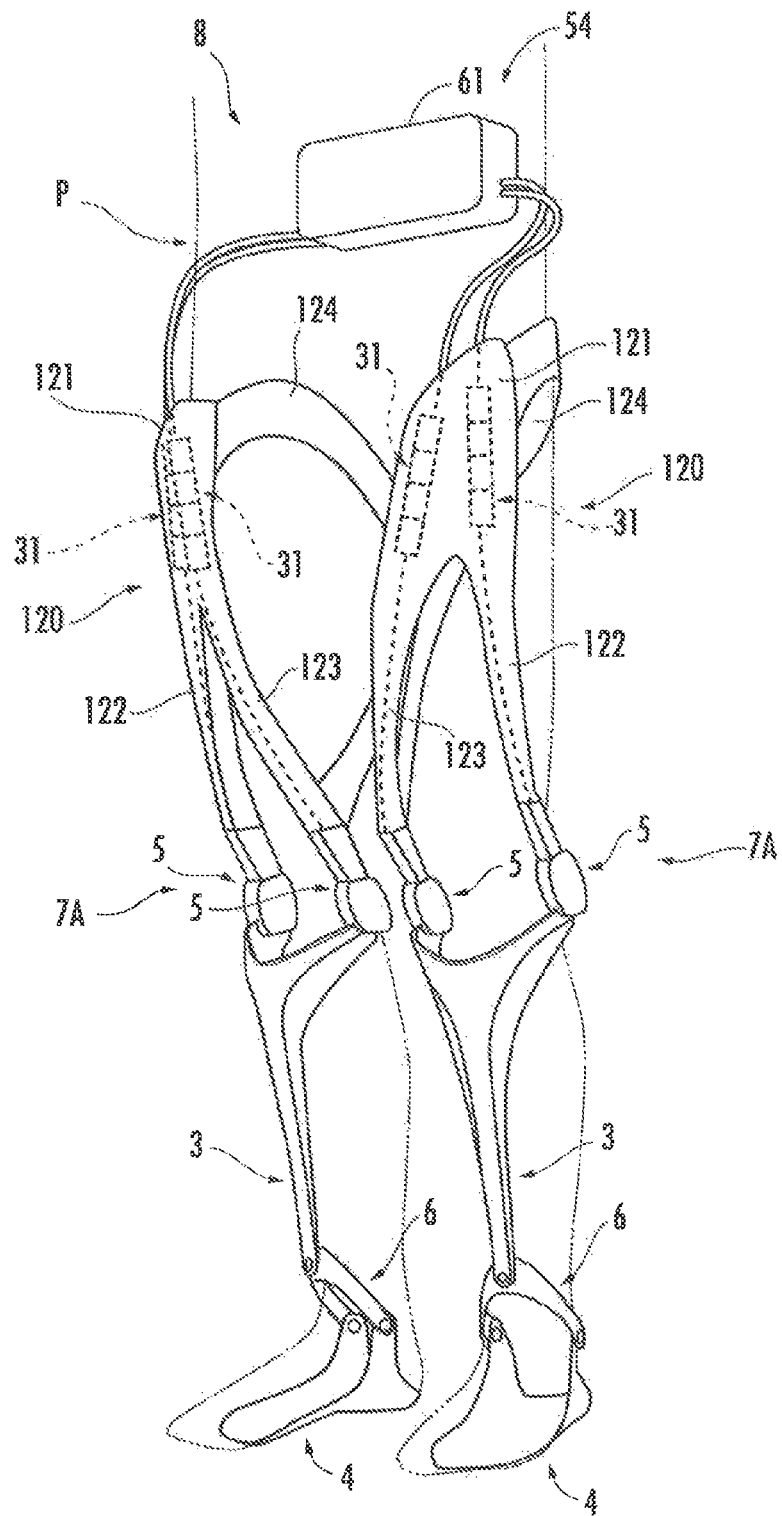

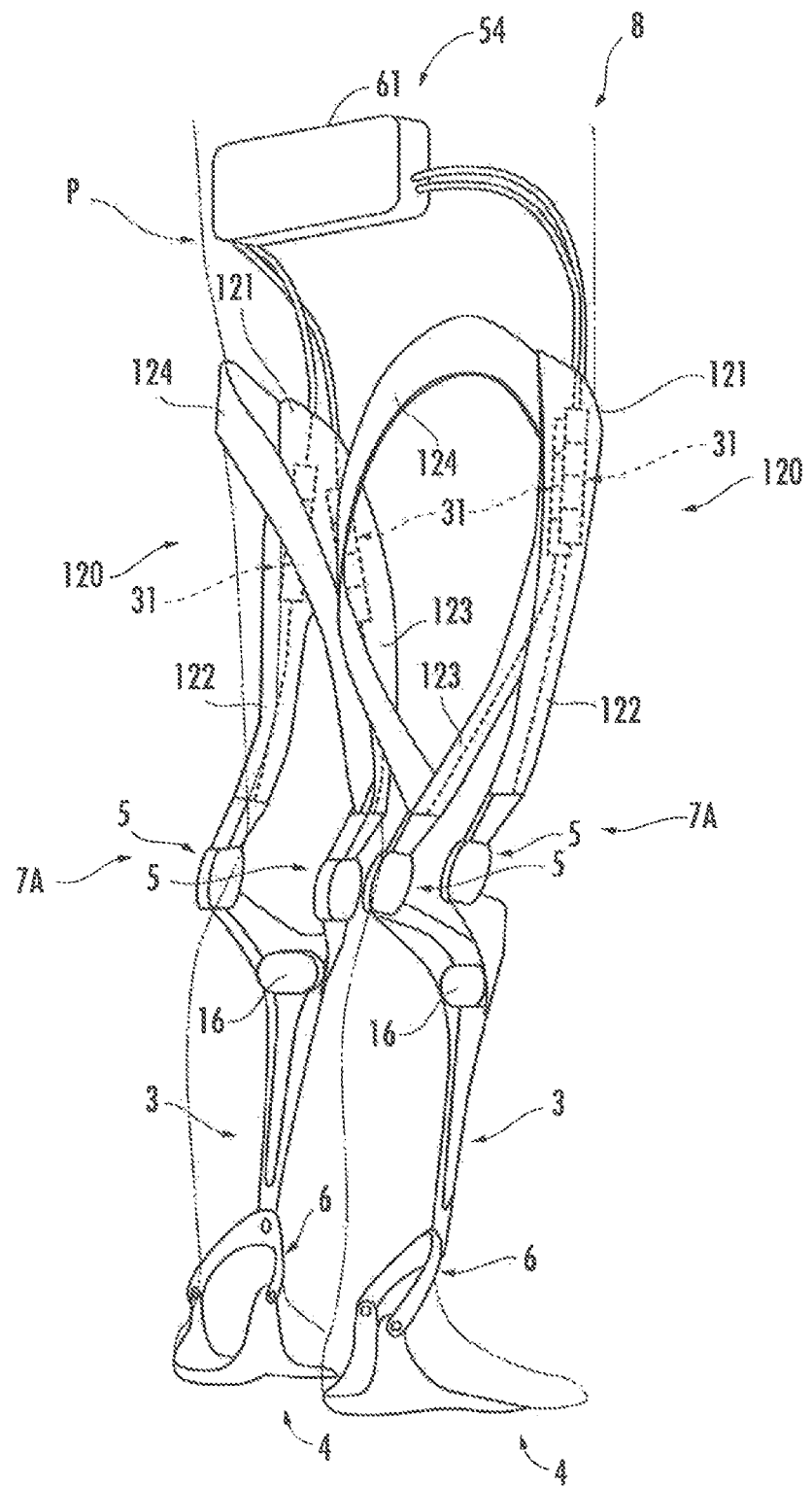

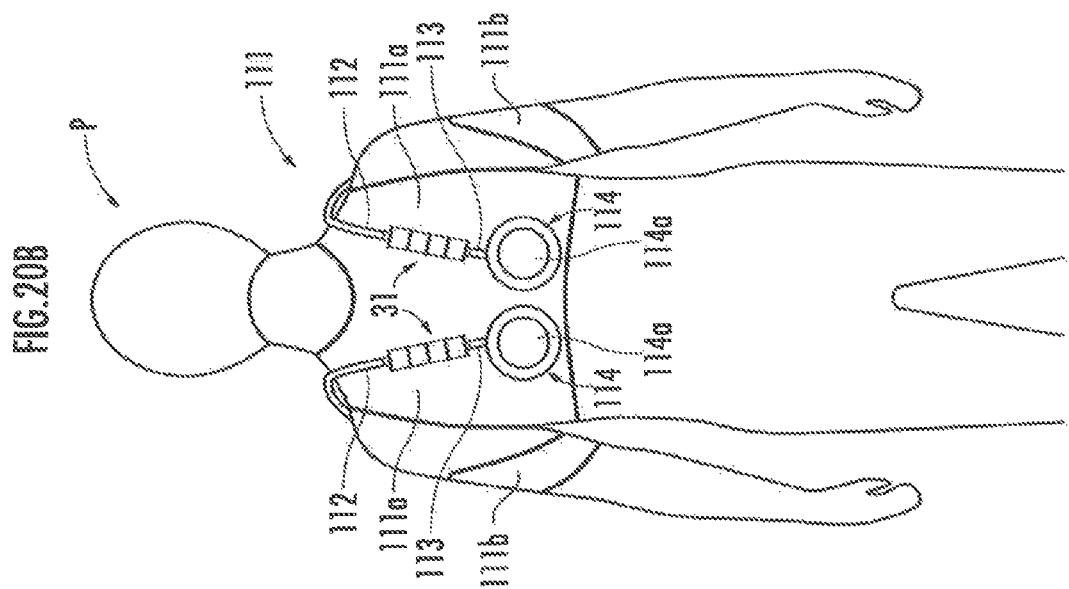

ELASTIC FORCE GENERATING DEVICE

BACKGROUND OF THE INVENTION

Field of the Invention

The present invention relates to a device that generates an elastic force.

Description of the Related Art

As a motion assisting apparatus for assisting, for example, the motion of a person to be assisted, there has hitherto generally been known one adapted to generate an elastic force for assisting the motion of a person to be assisted by using a tension spring, such as a coil spring. Motion assisting apparatuses configured to generate elastic forces for assisting the bending and stretching motions of the legs of a person to be assisted by tension springs are described in, for example, Japanese Patent Application Laid-Open No. 2012-100983 (hereinafter referred to as "Patent Document 1") and Japanese Patent Application Laid-Open No. 2014-508010 (hereinafter referred to as "Patent Document 2").

An attempt to enhance the stiffness of a tension spring, such as a coil spring, inevitably leads to an increased weight of the spring as well as an increased size thereof. For this reason, as indicated in Patent Documents 1 and 2, it is generally difficult to use springs with high stiffness as the tension springs to be mounted in a motion assisting apparatus to be attached to a person.

Since it is difficult to use a tension spring with high stiffness as described above, the amount of elongation of the spring has to be increased in order to have the spring generate a relatively large elastic force. This tends to lead to a larger space required for the elongation of the spring. Further, in order to secure a sufficient required amount of elongation of the spring, the natural length of the spring tends to also increase.

Accordingly, it is difficult for a tension spring, such as a coil spring, to successfully generate a large elastic force by a lightweight, compact configuration.

Meanwhile, an elastic member having a closed-cell structure (closed pore structure) incorporating hermetically sealed air chambers, such as, for example, a rubber sponge, allows an elastic force to be increased with high responsiveness to the compression thereof. It is therefore considered possible to generate a large elastic force with a lightweight, compact configuration by using such an elastic member.

However, in this type of elastic member, if the length in the direction of compression is increased to a certain extent so as to make it possible to secure a required variable range of an elastic force to be generated, then the elastic member is apt to give rise to an abnormal bending problem that, for example, the elastic member considerably bends and buckles at the time of compression. If such an abnormal bending problem takes place, then the elastic member is no longer capable of generating the required elastic force.

SUMMARY OF THE INVENTION

The present invention has been made in view of the background described above, and an object of the invention is to provide an elastic force generating device which uses a lightweight, compact elastic structure and which is capable of properly generating an elastic force by the compression of the elastic structure.

To this end, an elastic force generating device in accordance with the present invention includes: an elastic structure which is comprising of (or composed of) a multilayer construction formed by alternately stacking a plurality of elastic members, each of which incorporates one or more hermetically sealed air chambers, the volumes of which decrease by compression, and a plurality of partition plates having higher stiffness than that of the elastic members, which has through holes extending in the stacking direction, and the total length in the stacking direction is greater than a minimum width of each of the elastic members in a direction orthogonal to the stacking direction;

a flexible lengthy member inserted in the through hole of the elastic structure; and a tension imparting mechanism which is a mechanism adapted to variably impart a tension to the flexible lengthy member and which is adapted to transmit a force between the flexible lengthy member and the elastic structure such that, at the time of imparting a tension to the flexible lengthy member, a force for compressing the elastic structure in the stacking direction increases as the tension increases (a first aspect of the invention).

According to the elastic force generating device of the first aspect of the invention, the total length of the elastic structure in the stacking direction is greater than the minimum width of each of the elastic members in the direction orthogonal to the stacking direction. Hence, the elastic structure can be compressed not only in a state in which the stacking direction becomes substantially linear but can be also compressed in a state in which the elastic structure is locally or entirely bent to a certain extent.

If the elastic structure were comprising of only a single elastic member, then the elastic structure would easily develop an abnormal bending state, in which, for example, the elastic structure excessively bends (buckles), when the elastic structure is compressed.

According to the present invention, however, the elastic structure is formed of the multilayer construction formed by alternately stacking the elastic members and the partition plates having higher stiffness than that of the elastic members. Thus, the elastic structure according to the present invention prevents the abnormal bending state, such as the excessive bending of the elastic structure, from easily taking place at the time of compression, as compared with the case where the elastic structure is comprising of a single elastic member.

In addition, the flexible lengthy member, to which the tension is imparted by the tension imparting mechanism, is inserted in the through hole of the elastic structure (inserted to penetrate). Further, the tension imparting mechanism transmits the force between the flexible lengthy member and the elastic structure such that the force for compressing the elastic structure in the stacking direction increases (consequently increasing the amount of compression of the elastic structure) as the tension imparted to the flexible lengthy member increases, that is, the tension imparted to the flexible lengthy member increases concurrently as the elastic force from the compression of the elastic structure increases.

The flexible lengthy member, to which the tension of a magnitude matching the elastic force of the elastic structure is imparted, is inserted in the through hole of the elastic structure. Hence, even if the elastic structure becomes close to the abnormal bending state when the elastic structure is compressed, the flexible lengthy member makes it possible to prevent the elastic structure from reaching the abnormal bending state.

Further, the partition plates of the elastic structure may be sufficiently thinner than the elastic members. Therefore, the elastic structure is composed using the elastic members as its major constituent elements. This makes it possible to configure the lightweight, compact elastic structure capable of generating a large elastic force by compression with a relatively high sensitivity.

Thus, the elastic force generating device according to the first aspect of the invention allows the lightweight, compact elastic structure to be used to properly generate an elastic force by the compression of the elastic structure.

In the first aspect of the invention described above, the through hole of the elastic structure is preferably configured such that a minimum value of a cross-section area of the through hole in the partition plate is smaller than a minimum value of a cross-section area of the through hole in the elastic member (a second aspect of the invention).

With this arrangement, when the elastic structure is compressed or expanded from a compressed state, the flexible lengthy member can be prevented or restrained from coining in slide contact with the elastic members. This prevents or restrains a friction from taking place between the flexible lengthy member and the elastic members, or the flexible lengthy member from biting into the elastic members. Hence, when the elastic structure is compressed or expanded from the compressed state, an energy loss due to a friction between the elastic members and the flexible lengthy member can be prevented or restrained. Further, it is possible to prevent or restrain the elastic members from being damaged by the flexible lengthy member.

In the first aspect of the invention or the second aspect of the invention, preferably, the partition plate is formed such that a portion adjacent to an inner periphery around the through hole in the partition plate is thicker than that of a portion adjacent to an outer periphery of the partition plate, and that the elastic member is stacked on the portion adjacent to the outer periphery of the partition plate (a third aspect of the invention).

With this arrangement, the portion adjacent to the inner periphery of the partition plate is thicker, so that the length of the through hole (the length in the stacking direction the partition plate is greater. Hence, when the elastic structure is compressed or expanded from the compressed state, causing the flexible lengthy member to be pressed against the inner peripheral surface of the through hole in the partition plate, the contact pressure applied between the flexible lengthy member and the inner peripheral surface of the through hole in the partition plate is prevented or restrained from being concentrated at a local spot of the flexible lengthy member or the partition plate.

As a result, the durability of the flexible lengthy member or the partition plate can be enhanced. Further, the frictional force between the flexible lengthy member and the partition plate can be reduced, so that the energy loss attributable to the friction can be reduced.

Further, the elastic member is stacked on the portion adjacent to the outer periphery of the partition plate, thus preventing a gap (a gap in the stacking direction) from being formed between the portion adjacent to the outer periphery of the partition plate and the elastic member.

In the first to the third aspects of the invention described above, preferably, the inner peripheral surface of the through hole in the partition plate among the through holes of the elastic structure is formed in a curve such that the cross-section area of the through hole at a middle between both ends in the direction of the thickness of the partition plate is smaller than the cross-section area of the through hole at both ends in the direction of the thickness of the partition plate (a fourth aspect of the invention).

With this arrangement, when the elastic structure is compressed or expanded from the compressed state, causing the flexible lengthy member to be pressed against the inner peripheral surface of the through hole in the partition plate, the flexible lengthy member is easily curved along the inner peripheral surface of the through hole in the partition plate. Therefore, the contact pressure applied between the flexible lengthy member and the inner peripheral surface of the through hole in the partition plate is prevented or restrained from being concentrated at a local spot of the flexible lengthy member or the partition plate.

As a result, the durability of the flexible lengthy member or the partition plate can be enhanced. Further, the frictional force between the flexible lengthy member and the partition plate can be reduced, so that the energy loss attributable to the friction can be reduced.

Especially when the second aspect of the invention and the third aspect of the invention described above are combined, the foregoing effect can be further enhanced.

Further, in the first to the fourth aspects of the invention described above, the inner peripheral surface of the through hole in the partition plate among the through holes of the elastic structure is preferably comprising of a slide material (a fifth aspect of the invention).

With this arrangement, even if the flexible lengthy member and the partition plate come in slide contact when the elastic structure is compressed or expanded from the compressed state, the frictional force between the flexible lengthy member and the partition plate is reduced. Hence, the durability of the flexible lengthy member or the partition plate can be enhanced and the energy loss due to the friction can be reduced.

In the first to the fifth aspects of the invention described above, preferably, the elastic member is firmly fixed to the partition plate at its surface of contact with the partition plate (a sixth aspect of the invention).

This arrangement prevents the occurrence of a friction between the elastic member and the partition plate when the elastic structure is compressed or expanded from the compressed state. Hence, the occurrence of the energy loss due to the friction can be prevented.

The first to the fifth aspects of the invention described above may adopt a configuration in which the elastic member is in slide contact with the partition plate at its surface of contact with the partition plate (a seventh aspect of the invention).

This arrangement makes it possible to enhance the vibration attenuation performance of the elastic structure by making use of the friction that occurs between the elastic member and the partition plate when the elastic structure expands from the compressed state the accumulated elastic energy is released).

The first to the seventh aspects of the invention described above may adopt a configuration in which a guide tube which is extended in the stacking direction and externally inserted onto the elastic structure is further provided, and the elastic structure is disposed inside the guide tube such that the elastic structure is compressed in the stacking direction along an inner peripheral surface of the guide tube (an eighth aspect of the invention).

With this arrangement, the elastic structure is compressed along the inner peripheral surface of the guide tube. This makes it possible to further reliably prevent the occurrence of the abnormal bending state, such as the excessive bending of the elastic structure when the elastic structure is compressed.

In the eighth aspect of the invention, preferably, a maximum value of the cross-section area of the partition plate has a magnitude which allows the partition plate to come in slide contact with the inner peripheral surface of the guide tube, and the maximum value is larger than a maximum value of the cross-section area of the elastic member at the time of the compression of the elastic structure in ninth aspect of the invention).

This arrangement prevents or restrains the slide contact between the elastic member and the guide tube when the elastic structure is compressed or expanded from the compressed state. Consequently, the occurrence of the friction between the elastic member and the guide tube is prevented or restrained. This makes it possible to prevent or restrain the occurrence of the energy loss caused by the friction between the elastic member and the guide tube when the elastic structure is compressed or expanded from the compressed state.

Further, the eighth aspect of the invention or the ninth aspect of the invention described above may adopt a mode in which the guide tube is configured to be curvable or curved (a tenth aspect of the invention).

With this arrangement, the elastic structure and the guide tube can be disposed in a curved space. This permits a higher degree of freedom of choice of the place where the elastic structure and the guide tube are disposed.

The first to the tenth aspects of the invention described above may adopt a configuration that further includes a stretchable net or cover attached to the elastic structure so as to cover the outer peripheral surface of the elastic structure (an eleventh aspect of the invention).

According to the eleventh aspect of the invention, when the elastic structure expands or contracts, the elastic members of the elastic structure are prevented from directly coming in slide contact with a wall surface or the like around the elastic structure, and the elastic members come in slide contact with the wall surface or the like through the intermediary of the net or the cover, which covers the outer peripheral surface of the elastic structure. In this case, a material having a small friction coefficient (e.g. fluorine resin) can be used for the net or the cover, thus permitting a reduction in the friction that may occur between the elastic structure and the wall surface or the like around the elastic structure when the elastic structure expands or contracts.

The net or the cover is stretchable, so that a slide with a consequent friction hardly occurs between the net or the cover and the elastic members when the elastic structure expands or contracts.

The elastic force generating device according to the first to the eleventh aspects of the invention described above can be used as a device for applying an elastic force, which is generated by the compression of the elastic structure, to a joint mechanism that connects, for example, two members, namely, a first member and a second member, such that these two members can be relatively displaced.

In this case, the tension imparting mechanism may adopt, for example, the following configuration. If one of the both ends of the elastic structure in the stacking direction is defined as a first end and the other end thereof is defined as a second end, and a portion of the flexible lengthy member that is led out of a through hole of the elastic structure at a first end of the elastic structure is defined as a first lead-out portion and a portion thereof led out of the through hole of the elastic structure at the second end of the elastic structure is defined as a second lead-out portion, then the tension imparting mechanism may be configured to include, for example: a mechanism which binds the first lead-out portion to the first end of the elastic structure thereby to maintain a constant length of the first lead-out portion of the flexible lengthy member (hereinafter may be referred to as the "mechanism A"); a mechanism which maintains a constant distance between a portion on a way of a disposition path of the second lead-out portion of the flexible lengthy member and the second end of the elastic structure along the disposition path (hereinafter may be referred to as the "mechanism B"); and a mechanism which transmits a relative displacement motion of the second member to the second lead-out portion so as to cause the second lead-out portion of the flexible lengthy member to move with respect to the second end of the elastic structure according to the relative displacement motion of the second member with respect to the first member (hereinafter may be referred to as the "mechanism C") (a twelfth aspect of the invention).

With this arrangement, the tension imparting mechanism is provided with the mechanisms A, B and C, so that the elastic structure can be compressed or expanded from the compressed state according to the relative displacement motion of the second member with respect to the first member while a tension is being imparted to the flexible lengthy member. This makes it possible to apply the elastic force of the elastic structure to the joint mechanism as a force for driving or assisting the relative displacement of the second member with respect to the first member or for braking the relative displacement.

The twelfth aspect of the invention may adopt a mode in which the tension imparting mechanism is disposed, as an element that transmits the force between the flexible lengthy member and the elastic structure, to extend from the first end of the elastic structure and has a tube in which the first lead-out portion of the flexible lengthy member is inserted, and the tube is configured to be flexible while maintaining a length thereof constant (a thirteenth aspect of the invention).

With this arrangement, the flexibility of the tube permits a higher degree of freedom of the placement (layout) of the elastic structure and the constituent elements of the tension imparting mechanism or the choice of the constituent elements of the tension imparting mechanism. Hence, the elastic force generating device in accordance with the present invention can be applied to the joint mechanisms of a variety of types of apparatuses.

The tube that remains flexible while maintaining a constant length can be accomplished by a tube configured such that, for example, the tube exhibits high stiffness against a load in a longitudinal direction and exhibits low stiffness against a bending load.

The elastic force generating device according to the twelfth aspect of the invention or the thirteenth aspect of the invention can be used as, for example, a device that applies an elastic force generated by the compression of the elastic structure to a portion to be assisted, which is a leg, an arm or an upper body of a person, as an assisting force for assisting a bending and stretching of the portion to be assisted. In this case, the first member and the second member are attached to the portion to be assisted such that the first member and the second member are relatively displaced as the portion to be assisted bends or stretches (a fourteenth aspect of the invention).

With this arrangement, the bending or stretching of the portion to be assisted of a person can be assisted by the elastic force of the elastic structure. In this case, the elastic structure in accordance with the present invention can be made lightweight and compact as described above. Thus, it is possible to achieve a higher degree of freedom of the place of installation on the person and to suppress the feeling of a burden, discomfort or the like to the person when installed.

Further, in the foregoing fourteenth aspect of the invention, as an example, the first member and the second member may be comprising of a thigh frame and a crus frame, which are adapted to be attached to a person such that the thigh frame and the crus frame move integrally with a thigh and a crus, respectively, of a leg of the person as the thigh and the crus bend or stretch. In this case, the mechanism that transmits the relative displacement motion of the second member to the second lead-out portion may be configured such that the second lead-out portion of the flexible lengthy member travels in a direction for being drawn out of the through hole of the elastic structure as the degree of bending between the thigh and the crus of the leg increases (a fifteenth aspect of the invention).

With this arrangement, when a person wearing the thigh frame and the crus frame bends his or her leg at the knee, the degree of compression of the elastic structure increases as the degree of bending of the leg increases. This leads to an increase in the elastic force of the elastic structure. Thus, the elastic force makes it possible to generate an assisting force in the stretching direction of the leg.

The arrangement is capable of assisting the person with his or her motion when, for example, the person stands up from a squatting posture or from a chair or the like.

BRIEF DESCRIPTION OF THE DRAWINGS

FIG. 7 is a diagram illustrating the configuration of an actuator device provided in the joint power generating device illustrated in FIG. 5;

FIG. 8A to FIG. 8C are diagrams illustrating the operations performed when a person wearing the motion assisting apparatus in the embodiment bends and stretches;

FIG. 9 is a diagram for explaining the operation of the joint power generating device illustrated in FIG. 5;

FIG. 14 is a diagram illustrating an embodiment in which a stretchable net has been attached to the elastic structure;

FIG. 15 is a diagram illustrating the configuration of another example of the joint power generating device (the elastic force generating device) of the motion assisting apparatus in the embodiment;

FIG. 16 is a perspective view from the front side of a construction example of a leg link mechanism of the motion assisting apparatus;

FIG. 17 is a perspective view from a rear side of the construction example of the leg link mechanism of the motion assisting apparatus;

FIG. 20A and FIG. 20B are diagrams illustrating an example of how the elastic structures are attached in the case where the elastic forces of the elastic structures are applied to the upper portions (shoulders) of the arms of a person to be assisted.

DESCRIPTION OF THE PREFERRED EMBODIMENTS

An embodiment of the present invention will be described below with reference to FIG. 1 to FIG. 10.

Figure 1:
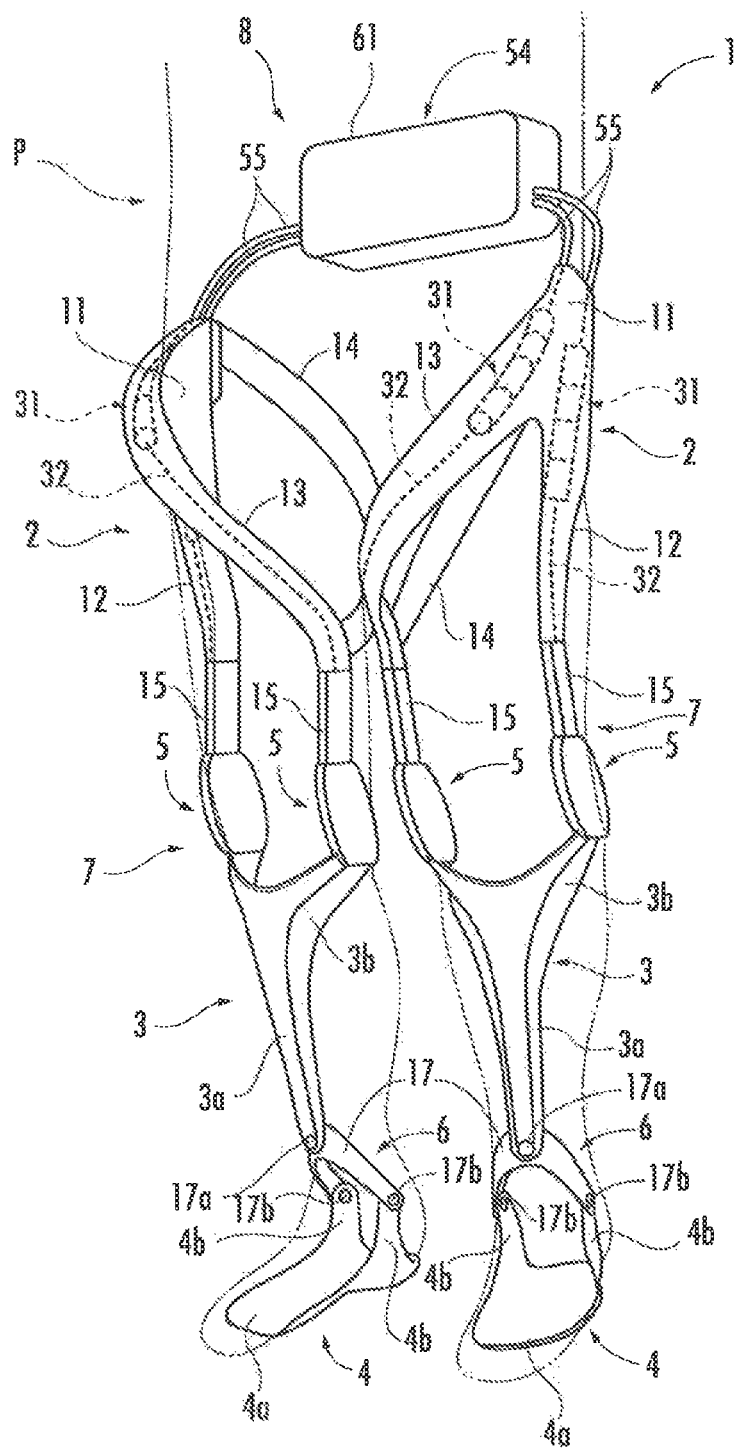
FIG. 1 is a perspective view from a front side of a motion assisting apparatus in an embodiment of the present invention.
Figure 2:
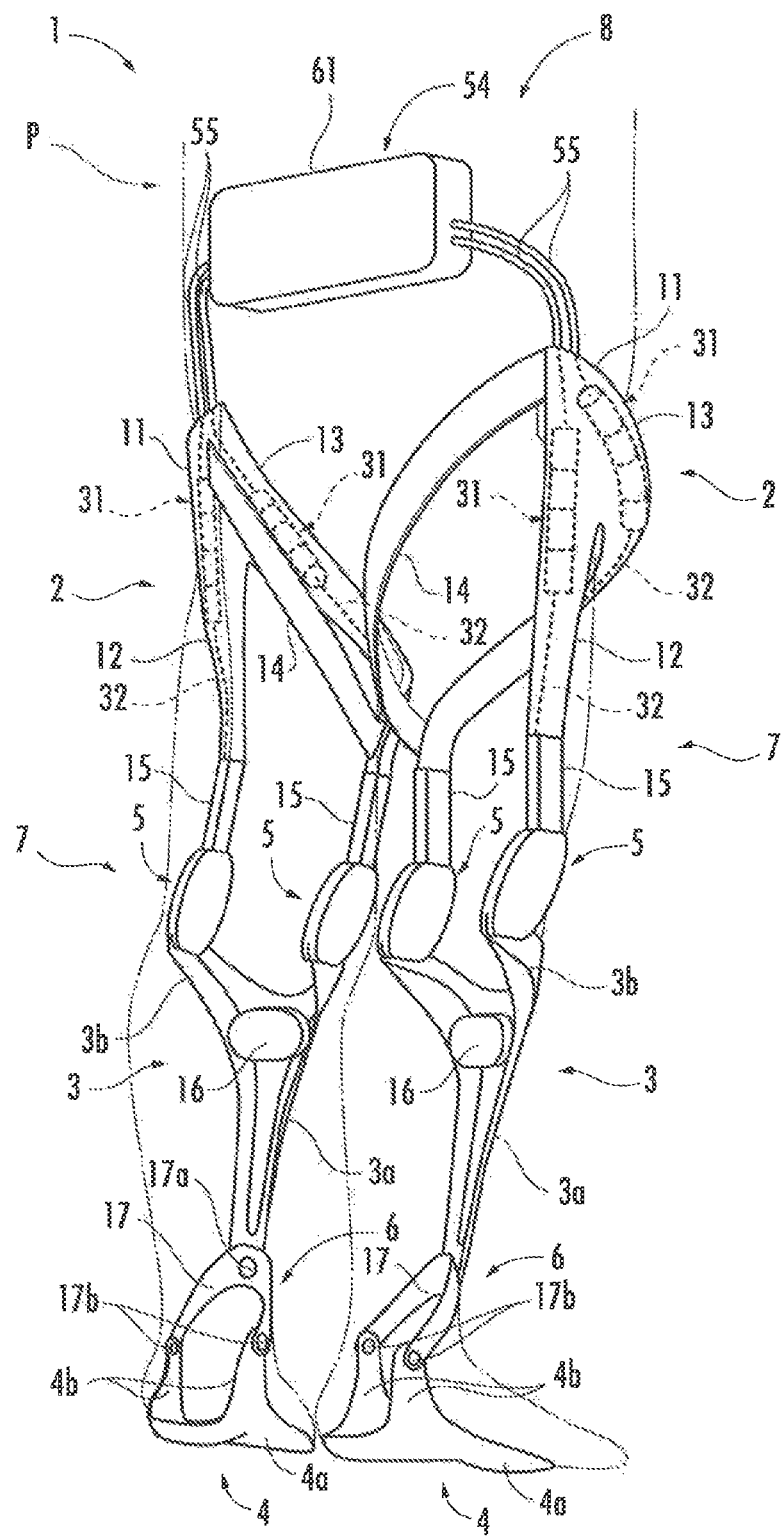
FIG. 2 is a perspective view from a rear side of the motion assisting apparatus in the embodiment.
Figure 3:
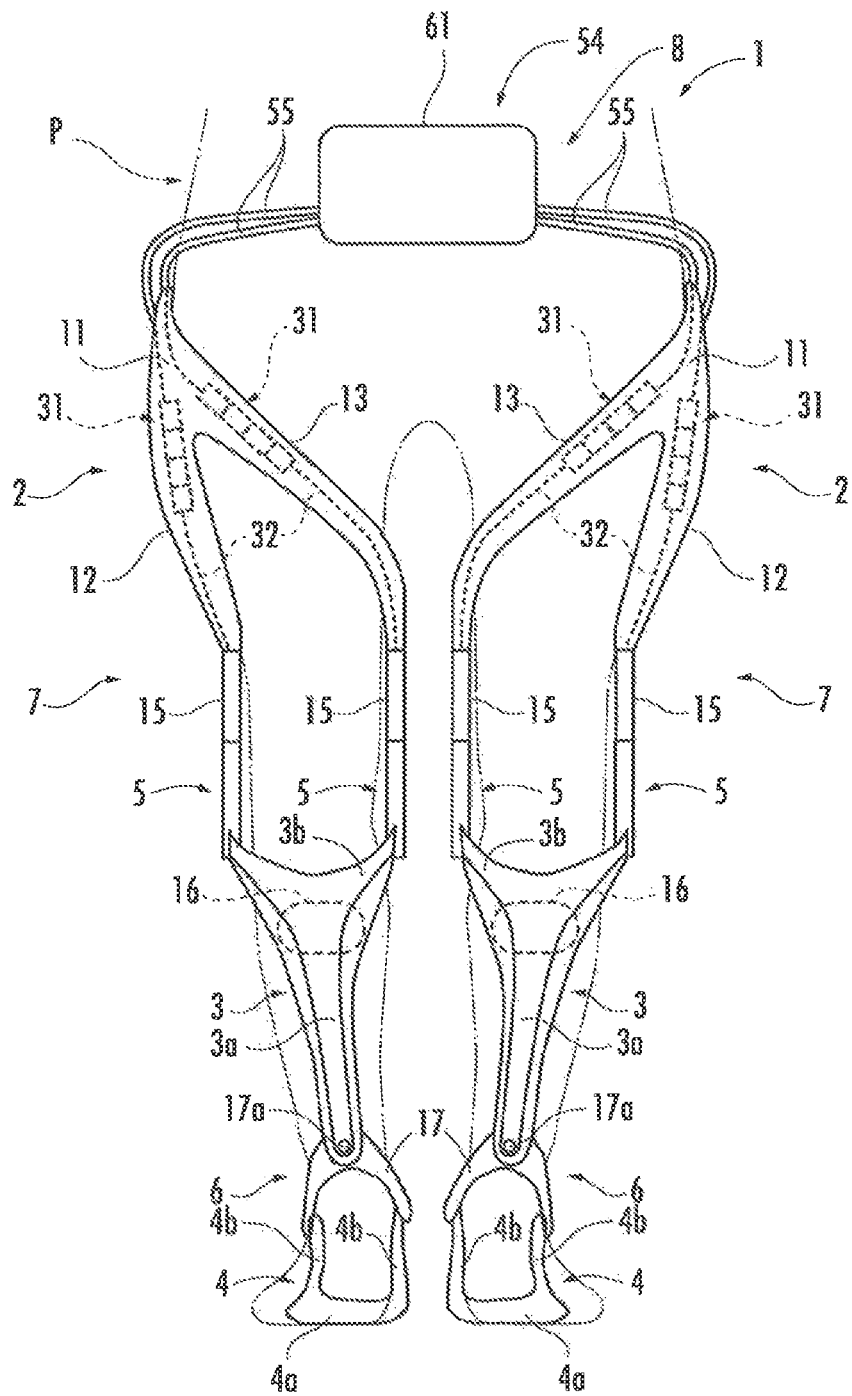
FIG. 3 is a front view of the motion assisting apparatus in the embodiment.

Referring to FIG. 1 to FIG. 3, an elastic force generating device illustrated in the present embodiment is a device provided in a motion assisting apparatus 1 to be attached to a person to be assisted P in order to assist the motions of his or her legs mainly when the person to be assisted P walks.

The motion assisting apparatus 1 has, for each leg of the person to be assisted P, a leg link mechanism 7 that includes a thigh frame 2, a crus frame 3, a foot frame 4, a pair of knee joint mechanisms 5, 5, which connect the thigh frame 2 and the crus frame 3 in a relatively displaceable manner, and an ankle joint mechanism 6, which connects the crus frame 3 and the foot frame 4 in a relatively displaceable manner, and a joint power generating device 8 that generates a joint power, which is a force to be imparted to the knee joint mechanisms 5, 5 of the leg link mechanism 7.

In the present embodiment, the joint power generating device 8 is an example of the elastic force generating device in accordance with the present invention. Further, the thigh frame 2 and the crus frame 3 correspond to the first member and the second member, respectively, in the present invention, and the knee joint mechanism 5 corresponds to the joint mechanism in the present invention. Further, each of the legs of the person to be assisted P corresponds to a portion to be assisted.

In FIG. 1 to FIG. 3, for the sake of simplicity each of the knee joint mechanisms 5 is schematically illustrated in a box shape, and the specific configuration of the knee joint mechanism 5 is not illustrated.

The leg link mechanism 7 for each leg of the person to be assisted P is attached to the leg such that each of the thigh frame 2, the crus frame 3 and the foot frame 4 moves integrally with each of the thigh, the crus and the foot of the leg (the right leg or the left leg) to which the leg link mechanism 7 is attached.

The phrase "the thigh frame 2 integrally moves with the thigh of the leg" means that the thigh frame 2 moves together with the thigh of the leg such that the position and the attitude of the thigh frame 2 relative to the thigh of the leg are maintained to be constant or substantially constant. In this case, the position or the attitude of the thigh frame 2 relative to the thigh of the leg may be allowed to slightly change (the thigh frame is slightly relatively displaced relative to the thigh of the leg) with the motion of the leg. This applies also to the phrase "each of the crus frame 3 and the foot frame 4 moves integrally with each of the crus and the foot."

The paired knee joint mechanisms 5, 5 of each of the leg link mechanisms 7 are disposed on both sides (namely, on the outer side and the inner side of the knee) in a lateral direction (namely, in the direction of a pitch axis) of the knee of the leg of the person to be assisted P when the leg link mechanism 7 is attached to the leg of the person to be assisted P.

In the following description, of the knee joint mechanisms 5, 5, the knee joint mechanism 5 disposed on the outer side of the knee may be referred to as the "outer knee joint mechanism 5" and the knee joint mechanism 5 disposed on the inner side of the knee may be referred to as the "inner knee joint mechanism 5."

Further, in the description of the present embodiment, of both sides in the lateral direction of the leg, the inner side and the outer side of each portion (namely, the knee, the thigh, and the like) of each leg of the person to be assisted P means the side closer to the other leg, i.e. the side opposing the other leg, and the side farther from the other leg, respectively. In other words, the inner side and the outer side of the right leg of the person to be assisted P are the left side and the right side, respectively, of the right leg, and the inner side and the outer side of the left leg are the right side and the left side, respectively, of the left leg.

Further, the terms "inner" and "outer" may be added to the designation of each element to distinguish between the elements associated with the inner knee joint mechanism 5 and the elements associated with the outer knee joint mechanism 5.

Further, in the description of the present embodiment, unless otherwise specified, the lateral direction (or the direction of the pitch axis), the longitudinal direction (or the direction of a roll axis), and the vertical direction (or the direction of a yaw axis) mean the lateral direction, the longitudinal direction, and the vertical direction, respectively, of the person to be assisted P when the person to be assisted P wearing the motion assisting apparatus 1 is standing substantially in an upright posture. Further, the pitch direction, the roll direction and the yaw direction mean the direction of rotation in the direction about the pitch axis, the direction of rotation in the direction about the roll axis, and the direction of rotation in the direction about the yaw axis, respectively.

The thigh frame 2 has, as its base frames, a first element frame 12 and a second element frame 13, which are bifurcated and extended from a base 11. The first element frame 12 and the second element frame 13 are configured to be integral and made of, for example, a resin member that is relatively hard.

The first element frame 12 and the second element frame 13 may alternatively be formed of a structure made by combining a plurality of members together into one piece.

The base 11, which is the root portion of the first element frame 12 and the second element frame 13, in the present embodiment is a portion which is disposed on one side of the waist at a height that is equal to or greater than the height of the inner base of the leg (i.e. the portion where the inner surfaces of both legs intersect with each other) of the person to be assisted P and lower than the hipbone. The base 11 in the present embodiment provides the upper end portion of the thigh frame 2. In this case, properly setting the vertical length of the thigh frame 2 allows the base 11 (the upper end portion of the thigh frame 2) to be disposed at the foregoing height.

The term "one side of the waist" refers to the right side of the waist in association with the thigh frame 2 of the leg link mechanism 7 for the right leg of the person to be assisted P, or refers to the left side of the waist in association with the thigh frame 2 of the leg link mechanism 7 for the left leg.

The first element frame 12 is an element frame that connects the base 11 to the outer knee joint mechanism 5. The first element frame 12 is configured to extend along the outer surface of the thigh of the person to be assisted P from the base 11 in the direction of the length of the thigh to the outer knee joint mechanism 5.

The second element frame 13 is an element frame that connects the base 11 to the inner knee joint mechanism 5. The second element frame 13 is configured to extend from the base 11 to the inner knee joint mechanism 5, passing the front surface curving toward the front surface side) of the thigh of the person to be assisted P.

Further, the second element frame 13 is configured to be inclined with respect to the thigh in the direction substantially toward the inner knee joint mechanism 5 from the base 11, as observed from the front side of the thigh of the leg of the person to be assisted P. In other words, the second element frame 13 is configured to extend to the inner knee joint mechanism 5 obliquely with respect to the thigh such that the second element frame 13 extends from the base 11 obliquely downward, as observed from the front side of the thigh of the leg of the person to be assisted P.

In this case, according to an example of the present embodiment, the second element frame 13 is configured such that the tilt of a portion thereof adjacent to the base 11 (namely, an upper portion and a portion thereof adjacent to the inner knee joint mechanism 5 (namely, a lower portion) relative to the direction of length of the thigh (i.e. the tilt as observed from the front side of the thigh) becomes smaller than that of a middle portion and that the tilt continuously and smoothly changes.

Further, the second element frame 13 is formed in a curved shape so as to smoothly curve obliquely along the curved surface on the front side of the thigh.

Further, the first element frame 12 and the second element frame 13 in the present embodiment are formed to be hollow inside so as to make it possible to accommodate an elastic structure 31 and the like, which will be discussed later.

Further, each of the first element frame 12 and the second element frame 13 has, at the lower end portion thereof, a hollow joint connection 15, which is a portion to be connected to the knee joint mechanism 5. The joint connection 15 is fixed to the upper portion of each of the first element frame 12 and the second element frame 13 (i.e., fixed to a portion on the upper side from the joint connection 15), or formed integrally with the upper portion. The joint connections 15, 15 at the lower end portions of the first element frame 12 and the second element frame 13 extend in substantially the same direction, namely, in the direction of the length of the thigh.

Further, the first element frame 12 and the second element frame 13 are connected to the outer knee joint mechanism 5 and the inner knee joint mechanism 5, respectively, through the joint connections 15 at the lower end portions thereof.

In the following description, the joint connection 15 at the lower end portion of the first element frame 12 may be referred to as the outer joint connection 15, and the joint connection 15 at the lower end portion of the second element frame 13 may be referred to as the inner joint connection 15.

The thigh frame 2 further includes a body support member 14 extended over between the base 11 and the lower portion of the second element frame 13. The body support member 14 is a member that functions to support the thigh of the person to be assisted P from the back side. The body support member 14 is disposed such that the thigh of the person to be assisted P can be inserted between the body support member 14 and the second element frame 13.

To be specific, the body support member 14 is extended over between the base 11 and the lower portion of the second element frame 13 such that the body support member 14 extends obliquely relative to the thigh and curves along the back of the lower portion of the buttock and the thigh of the person to be assisted P, extending from the base 11 obliquely downward in the direction toward the lower portion of the second element frame 13, as observed from the back side of the thigh of the person to be assisted P. Further, one end port on of the body support member 14 is connected to the base 11, while the other end portion thereof is connected to a lower portion of the second element frame 13, i.e., connected to a portion slightly above the inner joint connection 15 in the illustrated example.

In this case, the tilt of the body support member 14 with respect to the direction of the length of the thigh, i.e. the tilt as observed from the front side or the back side of the thigh, is substantially the same as the tilt of the second element frame 13 in the present embodiment.

Further, in the present embodiment, the body support member 14 is formed in a relatively thin belt shape so as to permit minimized sensation provoked by the foreign object corning in contact with the thigh or the buttocks when, for example, the person to be assisted P sits on a chair. Further, the body support member 14 has stiffness that is lower than that of the first element frame 12 and the second element frame 13. The body support member 14 is comprising of, for example, a resin member or a fabric member or the like that is softer than the first element frame 12 and the second element frame 13.

The crus frame 3 in the present embodiment has a base portion 3a, which is disposed to extend in the direction of the length of the crus on the front side of the crus of the person to be assisted P, and a forked portion 3b, which is integrally formed with the base portion 3a such that it extends from the upper portion of the base portion 3a to both sides (namely, the outer side and the inner side) of the knee of the person to be assisted P.

Further, of a pair of the distal ends of the forked portion 31), the distal end on the inner side of the knee is connected to the second element frame 13 of the thigh frame 2 through the intermediary of the inner knee joint mechanism 5. Further, of the pair of the distal ends of the forked portion 3b, the distal end on the outer side of the knee is connected to the first element frame 12 of the thigh frame 2 through the intermediary of the outer knee joint mechanism 5.

The upper portion of the base portion 3a (the base of the forked portion 3b), which has a relatively large area, is disposed to cover the upper front (specifically the tibial tuberosity) of the crus. The upper portion of the base portion 3a is the part to which the force of contact with the tibial tuberosity of the crus is applied when the leg of the person to be assisted P, for example, bends or stretches. Hence, a pad 16 comprising of a buffer member is fixed to the inner surface of the upper portion of the base portion 3a, as indicated by the dashed line in FIG. 3. Thus, the upper portion of the base portion 3a can be abutted against the tibial tuberosity of the person to be assisted P through the intermediary of the pad 16.

The foot frame 4 in the present embodiment is a plate-shaped frame having a bottom plate 4a, which is disposed on the bottom surface side of a foot of the person to be assisted P and on which the foot is rested. The bottom plate 4a is formed to have an insole shape that is substantially the same as a shoe insole shape or the shape of an insole with a part thereof cut off (e.g. the shape of an insole with a front part or a rear part thereof cut off).

Further, the foot frame 4 has rising portions 4b, 4b, which rise from both sides of a part of the bottom plate 4a that is adjacent to the heel. The rising portions 4b, 4b are connected to the lower end of the crus frame 3 (i.e. the lower end of the base portion 3a) through the intermediary of the ankle joint mechanism 6. The rising portions 4b, 4b are disposed to be positioned on the inner side and the outer side of the malleolus of the ankle of the person to be assisted P when the foot of the person to be assisted P is rested on the bottom plate 4a.

The ankle joint mechanism 6 includes a link member 17, which is disposed to encircle the front surrounding of the ankle of the person to be assisted P and which has a substantially semicircular shape (or a substantially U shape). A middle part of the link member 17 is connected to the lower end portion of the crus frame 3 through the intermediary of a joint shaft 17a in the direction of the roll axis.

Further, the link member 17 is pivotably supported such that the link member 17 can be relatively rotated in the roll direction about the axial center of the joint shaft 17a with respect to the crus frame 3.

The joint shaft 17a in the present embodiment is disposed to be positioned at a level that is higher than the lower joint of the talus of the ankle of the person to be assisted P when the foot of the person to be assisted P is placed on the bottom plate 4a of the foot frame 4. In the illustrated example, the joint shaft 17a is disposed to be positioned on the front side of the lower md portion of the crus of the person to be assisted P and above the instep of the foot.

Each of both ends of the link member 17 is connected to the rising portion 4b of the foot frame 4 through the intermediary of the joint shaft 17b in the direction of the pitch axis (more specifically, the rising portion 4b on the same inner or outer side of the heel of the person to be assisted P as the end portion of the link member 17). In this case, the joint shaft 17b on the inner side of the heel of the person to be assisted P and the joint shaft 17b on the outer side thereof are concentrically disposed. Further, the link member 17 is journaled such that the link member 17 can be relatively rotated with respect to the foot frame 4 about the axial centers of the joint shafts 17b and 17b on the inner side and the outer side (in the pitch direction).

The directions of the axial centers of the joint shafts 17b and 17b on the inner side and the outer side, respectively, will be supplementarily described. The rotational axes of the motions of the plantar flexion and the dorsiflexion of the ankle of the person to be assisted Pare generally slightly inclined relative to a plane orthogonal to the direction of the long axis of the tibia bone (i.e. the direction of the length of the crus).

Therefore, in the present embodiment, the axial centers of the joint shafts 17b, 17b of the ankle joint mechanism 6 are slightly inclined relative to the plane orthogonal to the direction of the long axis of the tibia bone (i.e. the direction of the length of the crus) of the person to be assisted P such that the axial centers thereof agree as much as possible with the rotational axes of the motions of the plantar flexion and the dorsiflexion of the ankle of the person to be assisted P. In this case, the axial centers of the joint shafts 17b, 17b of the ankle joint mechanism 6 are inclined such that the joint shaft 17b on the outer side is slightly lower than the joint shaft 17b on the inner side when the bottom plate 4a of the foot frame 4 is placed on a horizontal surface (or when the person to be assisted P wearing the motion assisting apparatus 1 is standing on a horizontal surface).

Since the ankle joint mechanism 6 is configured as described above, at the time of the motions of the plantar flexion and the dorsiflexion of the ankle of the person to be assisted P, the crus frame 3 and the foot frame 4 move integrally with the crus and the foot, minimizing the chance of the occurrence of relative displacements thereof with respect to the crus and foot of the person to be assisted P.

Further, the joint shaft 17a in the direction of the roll axis of the ankle joint mechanism 6 is disposed above the instep of the foot of the person to be assisted P, thus preventing the foot from interfering with the joint shaft 17a at the time of the motion of the plantar flexion of the ankle.

In the present embodiment, the ankle joint mechanism 6 does not have a joint shaft in the direction of the yaw axis (i.e. the vertical direction). However, if the foot of the person to be assisted P is rotated in the yaw direction relative to the crus, then the base portion 3a of the crus frame 3 is twisted. This enables the foot frame 4 to relatively rotate in the yaw direction with respect to the crus frame 3. Hence, the person to be assisted P can move without an impediment his or her foot to an arbitrary attitude with respect to the crus.

However, the ankle joint mechanism 6 may be configured to have a joint shaft in the direction of the yaw axis.

Both the outer knee joint mechanism 5 and the inner knee joint mechanism 5 are joint mechanisms sharing the same construction. Each of the knee joint mechanisms 5 in the present embodiment is configured to make it possible to accomplish the bending and stretching motions of the leg link mechanism 7 (i.e. the relative displacement motion between the thigh frame 2 and the crus frame 3) by the motions of the knee joint mechanisms 5, 5 in the same motional manner as the bending and stretching motions of a leg (i.e. the relative displacement motion between the thigh and the lower end portion) by the motions of the knee joint of an average person.

Figure 4:
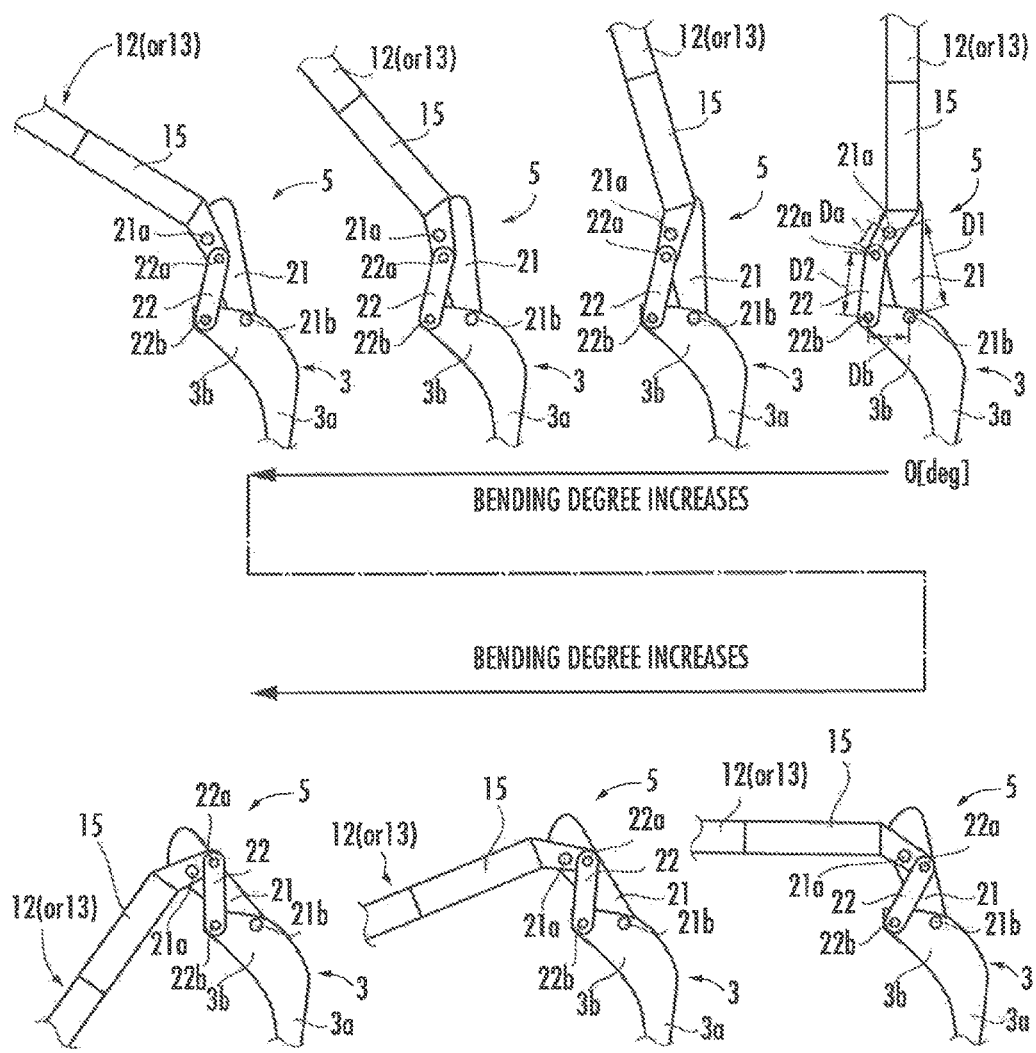
FIG. 4 is a diagram illustrating the configuration and the operation of a knee joint mechanism of the motion assisting apparatus in the embodiment.

Referring to FIG. 4, the following will describe a specific configuration of, for example, the outer knee joint mechanism 5 as a representative of the outer knee joint mechanism 5 and the inner knee joint mechanism 5. FIG. 4 illustrates, in addition to the configuration of the knee joint mechanism 5, the changes of the state of the knee joint mechanism 5 when the leg link mechanism 7 is bent from a stretched state thereof.

The outer knee joint mechanism 5 has a first link 21 and a second link 22, which are two links connecting a thigh frame 2 (specifically, the first element frame 12) and a crus frame 3 (specifically, the outer distal end portion of the pair of the distal end portions of the forked portion 3b).

The first link 21 is connected to the joint connection 15 at the lower end portion of the first element frame 12 of the thigh frame 2 through a joint shaft 21a. The first link 21 is also connected to the outer distal end portion of the forked portion 3b of the crus frame 3 through a joint shaft 21b. The joint shafts 21a and 21b have axial centers in the direction of the pitch axis, which are parallel to each other. Further, the first link 21 is journaled so as to be relatively rotatable in the pitch direction about the axial center of the joint shaft 21a with respect to the thigh frame 2. The first link 21 is also journaled so as to be relatively rotatable in the pitch direction about the axial center of the joint shaft 21b with respect to the crus frame 3.

The second link 22 is connected to the joint connection 15 at the lower end portion of the first element frame 12 of the thigh frame 2 through a joint shaft 22a. The second link 22 is also connected to the outer distal end portion of the forked portion 3b of the crus frame 3 through a joint shaft 22b. The joint shafts 22a and 22b have axial centers, which are parallel to each other and in the same direction (namely, the direction of the pitch axis) as that of the axial centers of the joint shafts 21a, 21b. Further, the second link 22 is journaled so as to be relatively rotatable in the pitch direction about the axial center of the joint shaft 22a with respect to the thigh frame 2. The second link 22 is also journaled so as to be relatively rotatable in the pitch direction about the axial center of the joint shaft 22b with respect to the crus frame 3.

The joint shaft 21b of the first link 21 that is adjacent to the crus frame 3 and the joint shaft 22b of the second link 22 that is adjacent to the crus frame 3 are disposed such that the joint shaft 22b is positioned farther to the rear than the joint shaft 21b.

Further, in the present embodiment, if the bending angle between the thigh frame 2 and the crus frame 3 is zero degrees, i.e. when the leg link mechanism 7 is stretched, then the joint shaft 22a of the second link 22 that is adjacent to the thigh frame 2 is positioned slightly farther to the rear side than the joint shaft 21a of the first link 21 that is adjacent to the thigh frame 2.

Further, as illustrated in FIG. 4, in the total of four joint shafts 21a, 21b, 22a and 22b of the first link 21 and the second link 22, if the interval between the axial centers of the joint shafts 21a and 21b is denoted by D1, the interval between the axial centers of the joint shafts 22a and 22b is denoted by D2, the interval between the axial centers of the joint shafts 21a and 22a is denoted by Da, and the interval between the axial centers of the joint shafts 21b and 22b is denoted by Db, then these D1, D2, Da and Db are set such that the relationships of expressions (1a) to (1c) given below hold.

$$D1 > Da \tag{1a}$$

$$D1 + Db > D2 + Da \tag{1b}$$

$$Da < Db \tag{1c}$$

The first link 21 and the second link 22 are disposed such that the positions thereof in the lateral direction (i.e. in the direction perpendicular to the paper surface of FIG. 4) are staggered so as not to interfere with each other when they are bent or stretched between the thigh frame 2 and the crus frame 3.

The above has described the detailed structure of the outer knee joint mechanism 5. The inner knee joint mechanism 5 has the same configuration as that of the outer knee joint mechanism 5. Further, in the inner knee joint mechanism 5, the joint connection 15 at the lower end portion of the second element frame 13 of the thigh frame 2 and the inner distal end portion of the forked portion 3b of the crus frame 3 are connected through the intermediary of the first link 21 and the second link 22.

In this case, the first link 21 of the inner knee joint mechanism 5 is journaled in a relatively rotatable manner by the joint connection 15 at the lower end portion of the second element frame 13 and the inner distal end portion of the forked portion 3b of the crus frame 3 through the intermediary of the joint shafts 21a and 21b, respectively.

Further, the second link 22 of the inner knee joint mechanism 5 is journaled in a relatively rotatable manner by the joint connection 15 at the lower end portion of the second element frame 13 and the inner distal end portion of the forked portion 3b of the crus frame 3 through the intermediary of the joint shafts 22a and 22b, respectively.

Further, the four joint shafts 21a, 21b, 22a and 22b in the inner knee joint mechanism 5 are disposed concentrically with the four joint shafts 21a, 21b, 22a and 22b, respectively, in the outer knee joint mechanism 5.

A supplementary description will be given of the directions of the axial centers of the four joint shafts 21a, 21b, 22a and 22b of each of the knee joint mechanisms 5. Preferably, the axial centers of the joint shafts 21a, 21b, 22a and 22b of each of the knee joint mechanisms 5 are slightly inclined with respect to the surface orthogonal to the direction of the long axis of the tibia bone, i.e. the direction of the length of the crus, in order for the thigh frame 2 and the crus frame 3 to integrally move with the thigh and the crus, respectively, of the person to be assisted P with a minimized chance of the occurrence of the relative displacement with respect to the thigh and the crus when a leg of the person to be assisted P bends or stretches.

Accordingly, in the present embodiment, the directions of the axial centers of the joint shafts 21a, 21b, 22a and 22b of each of the knee joint mechanisms 5 are slightly inclined with respect to the surface orthogonal to the direction of the length of the crus. In this case, the directions of the axial centers are inclined such that the joint shafts 21a, 21b, 22a and 22b of the inner knee joint mechanism 5 are lower than the joint shafts 21a, 21b, 22a and 22b, respectively, of the outer knee joint mechanism 5 when the person to be assisted P wearing the motion assisting apparatus 1 is standing on a horizontal surface.

Each of the inner knee joint mechanism 5 and the outer knee joint mechanism 5 is configured as described above. Hence, when the leg link mechanism 7 is bent or stretched at the knee joint mechanism 5, the first link 21 and the second link 22 of each of the knee joint mechanisms 5 move as the bending degree, i.e. the bending angle, of the crus frame 3 with respect to the thigh frame 2 increases, as illustrated in FIG. 4.

In this case, the first link 21 and the second link 22 of each of the knee joint mechanisms 5 move such that, as the bending angle of the crus frame 3 with respect to the thigh frame 2 increases from the angle in the state in which the leg link mechanism 7 is stretched (zero degrees), the upper joint shaft 21a of the first link 21 moves from a state in which the upper joint shaft 21a is positioned at the front side relative to the straight line connecting the joint shafts 22a and 22b of the second link 22, to a position at the rear side relative to the straight line via a state in which the upper joint shaft 21a is positioned on the straight line.

The motion of the knee joint mechanism 5 described above makes it possible to perform the relative displacement motion between the thigh frame 2 and the crus frame 3 in the bending or stretching motion of the leg link mechanism 7 in substantially the same manner as the relative displacement motion between the thigh and the crus in the bending or stretching motion of a leg of the person to be assisted P.

The leg link mechanisms 7 having the construction described above are attached to the person to be assisted P as illustrated in FIG. 1 and FIG. 2. In this case, each of the leg link mechanisms 7 is attached to the person to be assisted P by inserting the thigh of each leg of the person to be assisted P between the second element frame 13 of the thigh frame 2 of the leg link mechanism 7 corresponding to the leg and the body support member 14, and the foot of the leg is placed on the bottom plate 4a of the foot frame 4 such that the heel of the ankle of the leg is positioned between the pair of the rising portions 4b, 4b of the foot frame 4.

Thus, when the person to be assisted P wearing the leg link mechanisms 7 moves his or her legs, the thigh frame 2, the crus frame 3 and the foot frame 4 of each of the leg link mechanisms 7 attached to the legs move integrally with the thigh, the crus and the foot, respectively, of each of the legs.

FIG. 8A to FIG. 8C illustrate an example of the motion of each of the leg link mechanisms 7 when the person to be assisted P wearing the leg link mechanisms 7 bends his or her legs. FIG. 8A illustrates a state in which the person to be assisted P is standing upright (i.e. a state in which the legs are stretched), FIG. 8C illustrates a state in which the person to be assisted P is squatting (i.e. a state in which the legs are bent to a maximum), and FIG. 8B illustrates a state of the bent legs between the state of FIG. 8A and the state of FIG. 8C.

In each of the leg link mechanisms 7 according to the present embodiment, the motion of each of the knee joint mechanisms 5 having the constructions described above makes it possible to perform the relative displacement motion between the thigh frame 2 and the crus frame 3 in the bending or stretching motion of the leg link mechanism 7 in substantially the same manner as the relative displacement motion between the thigh and the crus in the bending or stretching motion of a leg of the person to be assisted P.

Hence, when the person to be assisted P bends or stretches his or her legs, the bending or stretching motion between the thigh frame 2 and the crus frame 3 is performed with a minimized chance of the occurrence of the relative displacements of the thigh frame 2 and the crus frame 3 with respect to the thigh and the crus, respectively, of each of the legs.

As a result, each of the knee joint mechanisms 5 is held at a position on the inner side or the outer side of the knee without jutting out to the front side of the knee from the position on the inner side or the outer side of the knee when the bending degree of the leg of the person to be assisted P is small and even when the bending degree is increased to a large degree, as seen by referring to FIG. 8A to FIG. 8G. Furthermore, even when the person to be assisted P kneels down, the knee joint mechanisms 5 will not come in contact with a floor, getting in the way.

Alternatively, the knee joint mechanism between the thigh frame 2 and the crus frame 3 can be comprising of, for example, a joint mechanism of a single-axis structure having the degree of freedom of rotation about one axis in the direction of the pitch axis.

In this case, however, the mismatch between the motion of the knee joint mechanism and the motion of the knee joint of a leg of the person to be assisted P tends to cause the relative displacements of the thigh frame 2 and the crus frame 3 with respect to the thigh and the crus, respectively, when the person to be assisted P bends the leg. This is apt to cause the person to be assisted P to feel his or her thigh and the crus being rubbed against the thigh frame 2 and the crus frame 3, respectively.

Further, the relative displacements of the thigh frame 2 and the crus frame 3 with respect to the thigh and the crus, respectively, cause the knee joint mechanism to jut out to the front side of the knee of the person to be assisted P especially when the bending degree of the leg of the person to be assisted P is increased. Hence, when the person to be assisted P tries to kneel down, the knee joint mechanism comes in contact with a floor, frequently getting in the way. The knee joint mechanisms 5 according to the present embodiment make it possible to obviate such an inconvenience.

If a footwear, such as a shoe or a slipper, is put on a foot of the person to be assisted P, then a mode may be adopted, in which, for example, the foot of the person to be assisted P with the footwear on is placed on the bottom plate 4a of the foot frame 4. An alternative mode may be adopted, in which the foot of the person to be assisted P is placed on the bottom plate 4a of the foot frame 4 and then the footwear is put on the bottom plate 4a and the foot. Further, the foot frame 4 may be combined with the footwear into one piece, i.e. making the foot frame 4 as part of the footwear.

The joint power generating device 8 as an example of the elastic force generating device in accordance with the present invention will now be described in detail. The joint power generating device 8 corresponding to each of the leg link mechanisms 7 of the motion assisting apparatus 1 includes two elastic structures 31, 31 configured to generate an elastic force by compression, flexible lengthy members 32 disposed, penetrating the elastic structures 31, and a tension imparting mechanism 33 which variably imparts tensions to the flexible lengthy members 32, as illustrated in FIG. 5.

Figure 5:
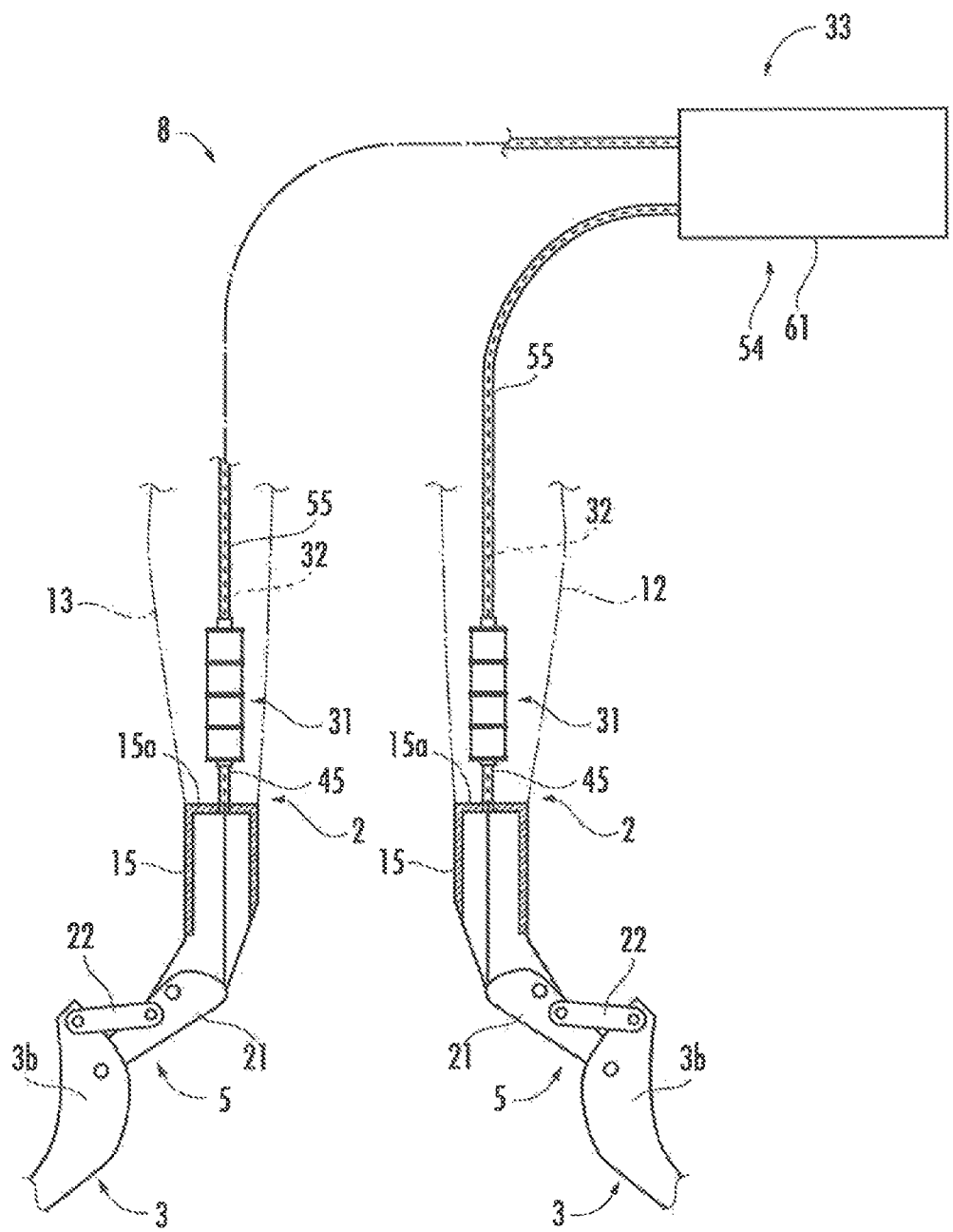
FIG. 5 is a diagram illustrating the configuration of a joint power generating device (an elastic force generating device) of the motion assisting apparatus in the embodiment.

For the simplicity of illustration, FIG. 5 illustrates the outer knee joint mechanism 5 and the inner knee joint mechanism 5 with their joint shafts facing in a direction perpendicular to the paper surface.

The flexible lengthy members 32 in the present embodiment are wires (linear members), and will be hereinafter referred to as "the wires 32."

One of the elastic structures 31, 31 is an elastic structure that generates an elastic force providing a joint power to be imparted to the outer knee joint mechanism 5 (hereinafter may be referred to as "the outer elastic structure 31"), while the other thereof is an elastic structure that generates an elastic force providing a joint power to be imparted to the inner knee joint mechanism 5 (hereinafter may be referred to as "the inner elastic structure 31"). The outer elastic structure 31 and the inner elastic structure 31 share the same construction. An example of the construction will be described with reference to FIG. 6A, FIG. 6B and FIG. 6C.

Each of the elastic structures 31 is a multilayer structure composed by alternately stacking a plurality of elastic members 41 and a plurality of partition plates 42. Further, a through hole 43, which penetrates the elastic structure 31 in the direction of stacking the elastic members 41 and the partition plates 42, is formed at the axial center of the elastic structure 31.

Each of the elastic members 41 in the present embodiment is formed in a cylindrical shape and is comprising of an elastic member incorporating many hermetically sealed air chambers (not illustrated), such as, for example, a closed-cell (closed-pore) rubber sponge. In this case, the direction of the axial center of each of the elastic members 41 is the stacking direction of the elastic structure 31. Further, the through hole of each of the elastic members 41 constitutes a part of the through hole 43 of the elastic structure 31.

Further, the minimum width of the elastic member 41 (the minimum value of the external width of the elastic member 41 in the direction orthogonal to the direction of the axial center of the elastic member 41) is set to be smaller than the full length in the stacking direction of the elastic structure 31.

Figure 6A:
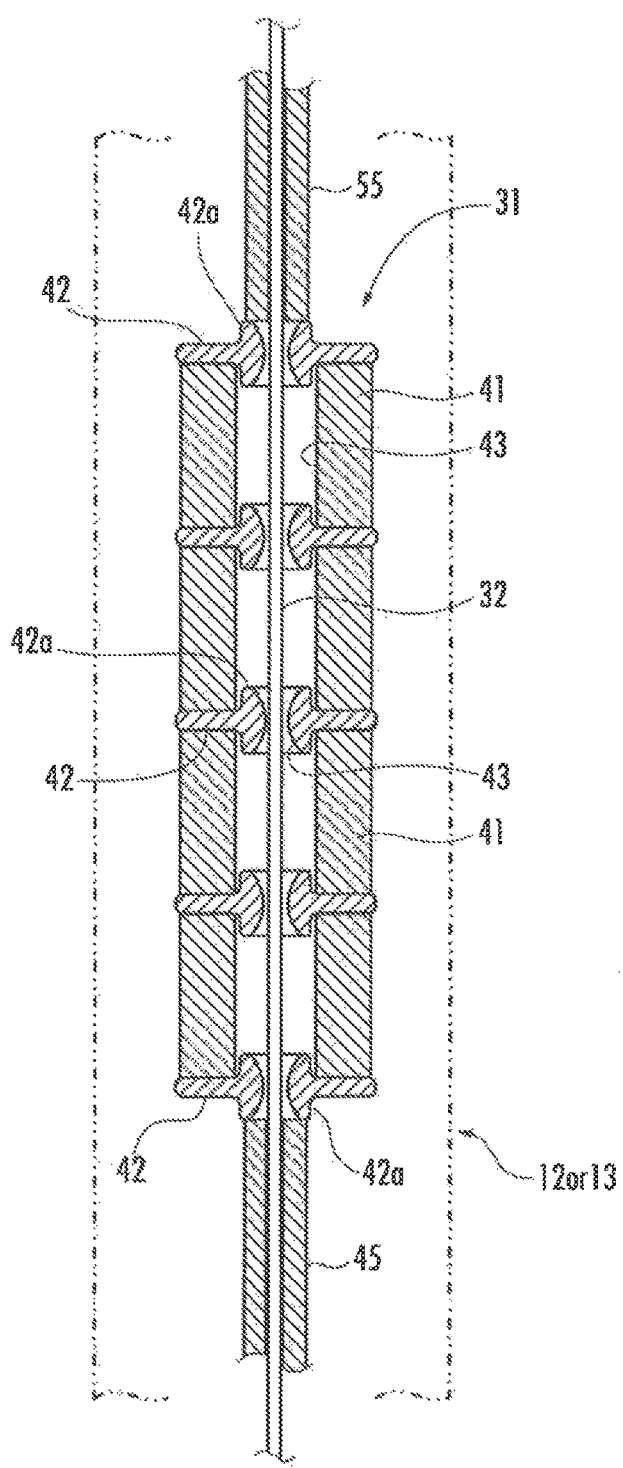
FIG. 6A is a sectional view of an elastic structure provided in the joint power generating device illustrated in FIG. 5.
Figure 6B:
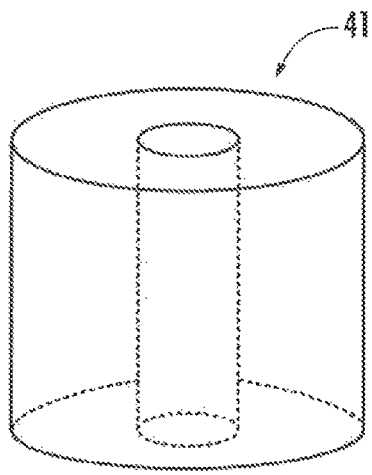
FIG. 6B is a perspective view illustrating an example of an elastic member provided in the elastic structure.

As an example, each of the elastic members 41 can be formed to have a cylindrical shape in a non-compressed state, i.e. in its natural state, as illustrated in FIG. 6B. In this case, the outside diameter (diameter) of the elastic member 41 is constant or substantially constant in the direction of the axial center of the elastic member 41, so that the outside diameter of the elastic member 41 coincides or substantially coincides with the minimum width and the maximum width of the elastic member 41. In this case, therefore, setting the outside diameter of the elastic member 41 to be smaller than the full length in the stacking direction of the elastic structure 31 makes the minimum width of the elastic member 41 smaller than the full length in the stacking direction of the elastic structure 31.

Each of the partition plates 42 is formed in an annular shape and comprising of a member having stiffness that is sufficiently higher than that of the elastic members 41, such as a metal or a hard resin. In this case, the direction of the axial center of each of the partition plates 42 (or the direction of the thickness thereof) is the stacking direction of the elastic structure 31. Further, the through hole of each of the partition plates 42 constitutes a part of the through hole 43 of the elastic structure 31.

The external shape and the area of each of the partition plates 42 observed in the direction of the axial center thereof, i.e. the direction of the thickness thereof, are set such that the entire or substantially entire end surface in the direction of the axial center of the elastic member 41 can be brought in contact with the end surface in the direction of the axial center of the partition plate 42, i.e. the surface on which the elastic member 41 is stacked.

Figure 6C:
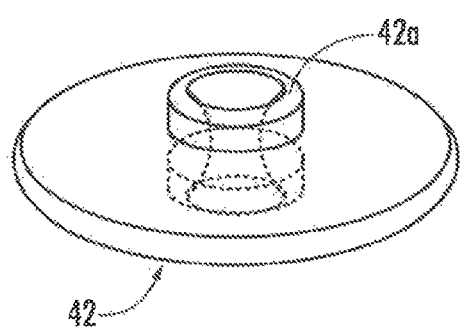
FIG. 6C is a perspective view illustrating an example of a partition plate provided in the elastic structure.

As an example, each of the partition plates 42 may be formed in the annular shape, as illustrated in FIG. 6C. Further, the outside diameters (diameters) of the partition plates 42 are set to coincide or substantially coincide with, for example, the outside diameters of the cylindrical elastic members 41, as illustrated in FIG. 6A.

Further, in the present embodiment, a portion 42a of each of the partition plates 42 that is adjacent to the inner periphery around the through hole is formed to be thicker than a portion surrounding the portion 42a, i.e. a portion adjacent to the outer circumference, as illustrated in FIG. 6C. The portion 42a (hereinafter referred to as "the thick portion 42a") projects to both sides in the direction of the thickness, i.e. the direction of the axial center, of the partition plate 42. Further, the thick portion 42a of each of the partition plates 42 is formed in a shape and a size that allows itself to be inserted in the end of the through hole of the elastic member 41 to be stacked on the partition plate 42.

For example, if the elastic members 41 are cylindrical, then the thick portion 42a of each of the partition plates 42 may be formed such that the external shape thereof (a circular shape in the illustrated example) observed in the direction of the axial center of the partition plate 42 is accommodated inside the cross-sectional shape of the through hole of the elastic member 41 (the shape thereof at the cross section orthogonal to the direction of the axial center of the elastic member 41), as illustrated in FIG. 6C. In this case, the maximum width (the diameter in the illustrated example) of the thick portion 42a is set to be slightly smaller than the width, i.e. the inside diameter, of the through hole of the elastic member 41.

Further, in the present embodiment, the minimum value of the cross-sectional area of the through hole of each of the partition plates 42, i.e. the area thereof at the cross section orthogonal to the direction of the axial center of the partition plate 42, is set to be smaller than the minimum value of the cross-sectional area of the through hole of the elastic member 41, i.e. the area thereof at the cross section orthogonal to the direction of the axial center of the elastic member 41).

In the present embodiment, the inner circumferential surface of the through hole of each of the partition plates 42 is formed in a curve such that the cross-sectional area of the through hole changes in the direction of the axial center, as illustrated in FIG. 6C.

More specifically, the inner circumferential surface of the through hole of the partition plate 42 is formed in a curve such that the cross-sectional area of the through hole of the partition plate 42 becomes a minimum at a middle position or substantially the central position between both ends (specifically, both ends in the direction of the axial center) of the thick portion 42a of the partition plate 42 and that the cross-sectional area of the through hole of the partition plate 42 increases toward both ends of the thick portion 42a of the partition plate 42. In other words, the inner circumferential surface of the through hole of the partition plate 42 is formed in a curve so as to be narrowed at the middle position in the direction of the axial center.

Further, the through hole of the elastic member 41 may be formed such that, for example, the cross-sectional area thereof remains constant in the direction of the axial center. In this case, minimum value of the cross-sectional area of the through hole of the partition plate 42, i.e. the cross-sectional area thereof at the middle position in the direction of the axial center of the partition plate 42, is set to be smaller than the constant cross-sectional area of the through hole of the elastic member 41.

Further, the inner circumferential surface of the through hole of the partition plate 42 is made of a slide material in order to reduce the coefficient of friction between the inner circumferential surface and the wire 32. As the slide material, a fluororesin, a copper alloy (phosphor bronze, brass or the like), or an oil-impregnated metal or the like may be used.

The elastic members 41 and the partition plates 42, which are configured as described above, are alternately stacked in a substantially coaxial manner thereby to constitute the elastic structure 31. In this case, the thick portion 42a of each of the partition plates 42 is inserted in the end of the through hole of the elastic member 41 stacked on the partition plate 42. Further, the through hole 43 of the elastic structure 31 is formed as the hole constituted by the through holes of the elastic members 41 and the through holes of the partition plates 42, which are in communication with each other.

Further, the contact surfaces of the elastic member 41 and the partition plate 42 that are stacked are firmly fixed to each other by, for example, an adhesive agent. More specifically, the contact surfaces are an end surface of the elastic member 41 and the end surface of the partition plate 42 in the direction of the thickness of the portion thereof adjacent to the outer circumference around the thick portion 42a, i.e. the portion that is thinner than the thick portion 42a. The stacked partition plate 42 and the elastic member 41 may be firmly fixed by a method other than bonding. For example, the stacked partition plate 42 and the elastic member 41 may be firmly fixed by, for example, baking or may be integrally molded.

In the present embodiment, the wire 32 is inserted in the through hole 43 of each of the elastic structures 31 configured as described above, and a tension is imparted to the wire 32, as will be described hereinafter. With the tension imparted to the wire 32 inserted in the through hole 43 as described above, each of the elastic structures 31 is compressed in the stacking direction. The elastic structure 31 generates an elastic force in the expanding direction according to the compression. The elastic force increases as the degree of the compression of the elastic structure 31 increases.

In the present embodiment, the elastic structure 31 configured as described above is installed to an appropriate place of the leg link mechanism 7, such as the thigh frame 2. More specifically, the outer elastic structure 31 and the inner elastic structure 31 are accommodated inside the first element frame 12 of the thigh frame 2 and inside the second element frame 13, respectively, as indicated by the dashed lines in FIG. 1 to FIG. 3.

In this case, each of the elastic structures 31 permits a bend to a certain extent due to the elastic deformation of the elastic members 41. Hence, if the place where the elastic structure 31 is to be installed in the first element frame 12 or the second element frame 13 is bent to a certain extent, then the elastic structure 31 can be installed to the installation place by being curved to fit the shape of the bent installation place. For example, in the motion assisting apparatus 1 according to the present embodiment, the inner elastic structure 31 is housed inside the second element frame 13 in the slightly curved state along the curved shape of the second element frame 13, as illustrated in FIG. 1 or FIG. 2.

The tension imparting mechanism 33 variably imparts a tension to the wire 32 inserted in the through hole 43 of each of the elastic structures 31.

In this case, the tension imparting mechanism 33 is configured to transmit the force between the wire 32 and the elastic structure 31 so as to cause the elastic structure 31 to generate an elastic force based on the tension imparted to the wire 32 inserted in the through hole 43 of the elastic structure 31 (an elastic force that balances the tension). Further, the tension imparting mechanism 33 is configured to be capable of changing the tension imparted to the wire 32 and the elastic force of the elastic structure 31 according to the relative displacement between the thigh frame 2 and the crus frame 3 (i.e. the bending or stretching motion of the leg link mechanism 7 caused by the motion of the knee joint mechanism 5). Further, the tension imparting mechanism 33 is configured to be also capable of imparting the elastic force of the elastic structure 31 as the joint power to the knee joint mechanism 5.

According to the present embodiment, the tension imparting mechanism 33 having the functions described above includes: a mechanism that binds a portion of the wire 32 led out from one end of the both ends in the direction of the axial center of each of the elastic structures 31 (hereinafter may be referred to as "the one-end-side led out portion") to one end of the elastic structure 31 thereby to maintain a constant length of the one-end-side led out portion: a mechanism that maintains a constant distance between a middle portion of the disposition path of a portion of the wire 32 led out from the other end of each of the elastic structures 31 (hereinafter may be referred to as "the other-end-side led out portion") and the other end of the elastic structure 31 along the disposition path; and a mechanism that transmits a relative displacement motion (the bending or stretching motion) of the crus frame 3 with respect to the thigh frame 2 to the other-end-side led out portion in order to cause the other-end-side led out portion of the wire 32 to move with respect to the other end of the elastic structure 31 according to the relative displacement motion.

In the present embodiment, the one end of each of the elastic structures 31 refers to the upper end of the elastic structure 31 (i.e. the end on the opposite side from the end closer to the knee joint mechanism 5), and the other end of the elastic structure 31 refers to the lower end of the elastic structure 31 (i.e. the end closer to the knee joint mechanism 5).

Supplementarily, in the present embodiment, the upper end (the one end) and the lower end (the other end) of the elastic structure 31 correspond to the first end and the second end, respectively, of the elastic structure in the present invention. Further, the one-end-side led out portion and the other-end-side led out portion of the wire 32 correspond to the first led out portion and the second led out portion, respectively, of the flexible lengthy member in the present invention.

A specific exemplary configuration of the tension imparting mechanism 33 will be described below. Referring to FIG. 5, the tension imparting mechanism 33 in the present embodiment includes, as a constituent element of a mechanism which maintains a constant distance along a disposition path of the other-end-side led out portion of the wire 32 between a middle portion of the disposition path and the lower end (the other end) of the elastic structure 31 (the mechanism corresponding to the foregoing mechanism 13), long thin tubes 45, one of which is disposed between a partition plate 42 at the lower end of the outer elastic structure 31 and a partition wall 15a at the upper end of the outer joint connection 15 in the first element frame 12 and the other of which is disposed between the partition plate 42 at the lower end of the inner elastic structure 31 and the partition wall 15a at the upper end of the inner joint connection 15 in the second element frame 13. In this case, the partition wall 15a of each of the joint connections 15 corresponds to the middle portion of the disposition path of the other-end-side led out portion of the wire 32.

Each of the tubes 45 is a guide tube in which the other-end-side led out portion of the wire 32 from the elastic structure 31 corresponding to the tube 45 is movably inserted.

One end of each of the tubes 45 is brought in contact with or fixed to the peripheral end portion of the opening end of the through hole of the partition plate 42 at the lower end of the elastic structure 31, and the other end of the tube 45 is brought in contact with or fixed to a predetermined portion of the partition wall 15a at the upper end of the joint connection 15. Each of the tubes 45 may alternatively be fixed to the thigh frame 2 (i.e. the first element frame 12 or the second element frame 13).

The inside of each of the tubes 45 is in communication with the through hole 43 of the elastic structure 31. The inside of the tube 45 is also in communication with the inside of the joint connection 15 through a hole formed in the partition wall 15a of the joint connection 15.

Further, the other-end-side led out portion of the wire 32 from each of the elastic structures 31 is inserted in the tube 45 connected to the lower end of the elastic structure 31. The other-end-side led out portion of the wire 32 is passed through the inside of the tube 45 to be led into the joint connection 15.

Each of the tubes 45 is comprising of, for example, a highly stiff member (e.g. a metal, a hard resin or the like). Hence, the distance between the lower end (the other end) of the outer elastic structure 31 and the partition wall 15a of the outer joint connection 15 (i.e. the distance along the disposition path of the wire 32) is maintained to be constant by the tube 45 between the outer elastic structure 31 and the partition wall 15a of the outer joint connection 15.

Similarly, the distance between the lower end (the other end) of the inner elastic structure 31 and the partition wall 15a of the inner joint connection 15 (i.e. the distance along the disposition path of the wire 32) is maintained to be constant by the tube 45 between the inner elastic structure 31 and the partition wall 15a of the inner joint connection 15.

Supplementarily, the tubes 45 may use tubes that have relatively low stiffness (i.e. have flexibility) against a bending load as long as the tubes exhibit high stiffness against a compression load in the direction of the length thereof.

Further, the mechanism that maintains the distance between the middle portion of the disposition path of the other-end-side led out portion of the wire 32 and the lower end, i.e. the other end, of the elastic structure 31 to be constant (i.e. the distance along the disposition path of the wire 32) is obviously not limited to the tubes 45 and may alternatively adopt a variety of configurations. For example, a configuration may be adopted, in which the partition plate 42 at the lower end of the outer elastic structure 31 and the partition plate 42 at the lower end of the inner elastic structure 31 may be directly fixed or immovably locked to the first element frame 12 and the second element frame 13, respectively. In this case, the tubes 45 may have low stiffness, i.e. may be soft. Alternatively, the tubes 45 may be omitted.

Further, the tension imparting mechanism 33 has a first link 21 of each of the knee joint mechanisms 5 as a constituent element of a mechanism (corresponding to the mechanism C) which transmits the relative displacement motion (i.e. a bending or stretching motion) of the crus frame 3 with respect to the thigh frame 2 to the other-end-side led out portion so as to cause the other-end-side led out portion of the wire 32 from each of the elastic structures 31 to move with respect to the lower end, i.e. the other end, of the elastic structure 31 according to the relative displacement motion. Thus, the first link 21 of each of the knee joint mechanisms 5 serves also as a constituent element of the tension imparting mechanism 33.

More specifically, according to the present embodiment, the first link 21 of each of the knee joint mechanisms 5 is formed such that the outer peripheral portion thereof (in other words, the portion having an interval, i.e. a moment arm length, relative to the joint shaft 21a) functions as the outer peripheral portion of the pulley. Further, in each of the first link 21 on the outer side and the first link 21 on the inner side, the end of the other-end-side led out portion of the wire 32, which has been led into the joint connection 15 from each of the elastic structures 31 is fixed to the outer peripheral portion of the first link 21 of the knee joint mechanism 5.

With this arrangement, the first link 21 of each of the knee joint mechanisms 5 rotates about the axial center of the joint shaft 21a with respect to the thigh frame 2 as the relative displacement motion (i.e. the bending or stretching motion of the leg link mechanism 7) of the crus frame 3 with respect to the thigh frame 2 is carried out, thereby increasing or decreasing the amount of the other-end-side led out portion of the wire 32 to be wound at the first link 21. This causes the other-end-side led out portion of the wire 32 to move with respect to the lower end of the elastic structure 31 corresponding to the wire 32.

The tension imparting mechanism 33 further includes an actuator device 54 for controlling the movement of the wire 32 and a tube 55 disposed between the partition plate 42 at the upper end of each of the elastic structure 31 and a chassis

61 of the actuator device 54 as the constituent elements of the mechanism (the mechanism corresponding to the mechanism A) that binds the one-end-side led out portion of the wire 32 from each of the elastic structures 31 to the upper end, i.e. the one end, of the elastic structure 31 in order to maintain a constant length of the one-end-side led out portion.

The chassis 61 of the actuator device 54 is attached to the person to be assisted P at a place where the chassis 61 does not interfere with the motion of the person to be assisted P. For example, as illustrated in FIG. 1 or FIG. 2, the chassis 61 is attached through the intermediary of a belt or the like (not illustrated) to an upper side of the waist on the back of the person to be assisted P such that the chassis 61 moves substantially together with the upper body of the person to be assisted P. Alternatively, the chassis 61 may be attached to, for example, the back of the person to be assisted P or to the upper body on the abdomen side.

Each of the tubes 55 is a guide tube in which the one-end-side led out portion of the wire 32 from the elastic structure 31 corresponding to the tube 55 is movably inserted.

The tube 55 between the outer elastic structure 31 and the chassis 61 is disposed to pass through the inside of the first element frame 12 from the upper end of the outer elastic structure 31 to the base 11 and further pass through the space outside the thigh frame 2 from the base 11 until reaching the chassis 61.

Further, the tube 55 between the inner elastic structure 31 and the chassis 61 is disposed to pass through the inside of the second element frame 13 from the upper end of the inner elastic structure 31 to the base 11 and further pass through the space outside the thigh frame 2 from the base 11 until reaching the chassis 61.

Then, one end of each of the tubes 55 is brought in contact with or fixed to the peripheral portion of the opening end of the through hole of the partition plate 42 at the upper end of the elastic structure 31, while the other end of the tube 55 is brought in contact with or fixed to a predetermined portion of the outer wall of the chassis 61.

Each of the tubes 55 has a length that is set to be greater than the linear distance between the upper end of the elastic structure 31 and the chassis 61 such that the tube 55 can be bent between the elastic structure 31 and the chassis 61 as the elastic structure 31 is compressed. Further, each of the tubes 55 is configured so as to exhibit relatively low stiffness against a bending load, and relatively high stiffness (i.e. high resistance to expansion and contraction) against a compression load in the direction of the length of the tube 55. The tubes 55 may use, for example, tubes having the same configuration as a brake tube of a bicycle, which is a tube comprising of a densely wound metal coil covered with a resin.

Further, the inside of each of the tubes 55 is in communication with the through hole 43 of the elastic structure 31. The inside of the tube 55 is also in communication with the inside of the chassis 61 through a hole formed in the chassis 61.

Further, the one-end-side led out portion of the wire 32 from each of the elastic structures 31 is inserted in the tube 55 connected to the upper end of the elastic structure 31. The one-end-side led out portion of the wire 32 is further passed through the inside of the tube 55 to be led into the chassis 61.

Supplementarily, the tubes 55 correspond to the tubes in the present invention.

As illustrated in FIG. 7, the actuator device 54 has, in the chassis 61, two pulleys 62, 62 around which the one-end-side led out portion of the wire 32 from the outer elastic structure 31 and the one-end-side led out portion of the wire 32 from the inner elastic structure 31 are wound, an electric motor 66 capable of rotatively driving the pulleys 62, 62, and a control unit 67 which controls the operation of the electric motor 66. Further, although not illustrated, a power source, such as a battery assembly, for the electric motor 66 and the control unit 67 is also installed in the chassis 61. Alternatively, however, the control unit 67 or the power source may be disposed at a place separate from the chassis 61 of the actuator device 54.

FIG. 7 illustrates only the actuator device 54 for one leg link mechanism 7 attached to either the left leg or the right leg of the person to be assisted P. The chassis 61 may be shared between or separately provided for the actuator device 54 for the leg link mechanism 7 to be attached to the left leg of the person to be assisted P and the actuator device 54 for the leg link mechanism 7 to be attached to the right leg.

The pulleys 62, 62 are concentrically connected such that they can be integrally rotated. Further, the end of the one-end-side led out portion of the wire 32 from the outer elastic structure 31 and the end of the one-end-side led out portion of the wire 32 from the inner elastic structure 31 are fixed to the outer peripheral portions of the pulleys 62.

The housing of the electric motor 66, i.e. the part to which the stator of the electric motor 66 is fixed, is secured to the chassis 61. Further, the pulleys 62, 62 are connected, through the intermediary of a reduction gear 63, to the output shaft of the electric motor 66 so as to allow an output torque of the electric motor 66 to be transmitted to the pulleys 62, 62.

The actuator device 54 is configured as described above, so that if the pulleys 62, 62 are held in a non-rotation state in the chassis 61 by the electric motor 66, then the one-end-side led out portions of the wires 32 from the elastic structures 31 are bound, through the intermediary of the chassis 61 and the tubes 55, to the upper ends, i.e. the one ends, of the elastic structures 31 such that the lengths of the one-end-side led out portions are maintained to be constant.

The control unit 67, which controls the operation of the electric motor 66, is comprising of an electric circuit unit that includes a CPU, a RAM, a ROM, an interface circuit and the like. The control unit 67 may alternatively be comprising of a plurality of electronic circuit units capable of mutual communication.

The control unit 67 according to the present embodiment receives the detection signals from a rotation sensor 71 that outputs signals based on the rotational angles of the pulleys 62, 62 and a ground contact sensor 72 that outputs signals based on whether the leg link mechanisms 7 attached to the legs of the person to be assisted P are in contact with a ground (i.e. whether a leg or legs of the person to be assisted P to which the leg link mechanisms 7 are attached is or are in a support leg state or a free leg state).

The rotation sensor 71 may be comprising of, for example, a rotary encoder, a potentiometer or the like installed to one of the pulleys 62, 62 or the electric motor 66 or the like. Further, the ground contact sensor 72 may be comprising of, for example, a force sensor or the like installed to the foot frame 4 so as to detect the pressure between the foot frame 4 and the sole of a foot of the person to be assisted P.

Further, the control unit 67 controls the operation of the electric motor 66 by executing a preinstalled program while monitoring the detection signals of the rotation sensor 71 and the ground contact sensor 72.

A description will now be given of the operation of the motion assisting apparatus 1 according to the present embodiment.

With the leg link mechanism 7 attached to each of the legs of the person to be assisted P as illustrated in FIG. 1 or FIG. 2, the control unit 67 is actuated.

For each of the leg link mechanisms 7, the control unit 67 controls the operation of the electric motor 66 as described below according to the detection signals of the rotation sensor 71 and the ground contact sensor 72.

If the detection signal of the ground contact sensor 72 indicates that the leg link mechanism 7 is not in contact with the ground, i.e. if the leg to which the leg link mechanism 7 is attached is a free leg, meaning that the foot frame 4 is moving in the air, then the control unit 67 controls the output torque of the electric motor 66 such that a small torque (e.g. a torque of a predetermined value) that permits the prevention of a slack in the wire 32 is imparted to the pulley 62.

In this case, when the leg to which the leg link mechanism 7 is attached is bent or stretched, causing the leg link mechanism 7 to bend or stretch at the knee joint mechanism 5, the wire 32 penetrating the elastic structure 31 moves relative to the elastic structure 31. In this situation, the tension of the wire 32 is maintained to a low tension that prevents the wire 32 from slacking.

More specifically, as the degree of bending of the leg link mechanism 7 at the knee joint mechanism 5 increases, the wire 32 penetrating the elastic structure 31 is pulled to be wound around the outer periphery of the first link 21 of the knee joint mechanism 5, causing the pulley 62 of the actuator device 54 to rotate in the direction for pulling out the wire 32. Thus, the wire 32 runs in the direction in which the length of the other-end-side led out portion from the elastic structure 31 increases.

Further, as the degree of bending of the leg link mechanism 7 at the knee joint mechanism 5 decreases, the wire 32 penetrating the elastic structure 31 is pulled out from the outer periphery of the first link 21 of the knee joint mechanism 5. Then, the pulley 62 of the actuator device 54 rotates in the direction for winding the wire 32. Thus, the wire 32 runs in the direction in which the length of the other-end-side led out portion from the elastic structure 31 decreases.

As described above, in the situation in which the wire 32 runs with respect to the elastic structure 31 as the leg link mechanism 7 bends or stretches, a compression load is not substantially applied to the elastic structure 31, so that the elastic force of the elastic structure 31 is not substantially applied to the knee joint mechanism 5.

Therefore, the person to be assisted P can move the leg in the free leg phase in the same manner as a normal motion manner as if the leg link mechanism 7 were not attached to the leg.

Meanwhile, if the detection signal of the ground contact sensor 72 indicates that the leg link mechanism 7 is in contact with the ground, i.e. if the leg to which the leg link mechanism 7 is attached is in the support leg phase (meaning that the foot frame 4 is in contact with the ground), then the control unit 67 controls the output torque of the electric motor 66 according to a detection signal of the rotation sensor 71 such that the rotational angle of the pulley 62 indicated by the output of the rotation sensor 71 is held at a constant angle, i.e. the pulley 62 is held in the non-rotation state.

When the output torque of the electric motor 66 is controlled as described above, the one-end-side led out portion of the wire 32 from the elastic structure 31 will be locked with respect to the chassis 61 through the intermediary of the pulley 62 and the electric motor 66. Further, the one-end-side led out portion of the wire 32 will be bound to the partition plate 42 at the upper end of the elastic structure 31 through the intermediary of the chassis 61 and the tube 55, thereby maintaining the length thereof to be constant.

In this condition, as the degree of bending of the crus frame 3 relative to the thigh frame 2, i.e. as the leg link mechanism 7 is bent at the knee joint mechanism 5 from a stretched state, the tube 55 corresponding to the elastic structure 31 bends and the elastic structure 31 is compressed, thus maintaining the length of the one-end-side led out portion of the wire 32 from the elastic structure 31 to be constant, as illustrated in FIG. 9.

At the same time, the output torque of the electric motor 66 is controlled such that the tension imparted to the wire 32 penetrating the elastic structure 31 increases to balance the elastic force generated by the compression of the elastic structure 31. In this case, the force between the wire 32 and the elastic structure 31 is transmitted through the intermediary of the pulley 62, the electric motor 66, the chassis 61 and the tube 55.

Thus, the elastic force of the elastic structure 31 will be imparted as the joint power in the direction for stretching the leg link mechanism 7 to the knee joint mechanism 5 on the same side (the outer side or the inner side) as the elastic structure 31. In this case, the amount of compression of the elastic structure 31 and the resultant elastic force increase as the degree of bending between the thigh frame 2 and the crus frame 3 increases.

As described above, the joint power from the elastic force of the elastic structure 31 is imparted to the knee joint mechanism 5 of the leg link mechanism 7 on the support leg side of the person to be assisted P, thus reducing the load on the support leg of the person to be assisted P when, for example, the person to be assisted P walks, stands up or sits down, squats or stands up from a squatting posture. This makes it possible to assist the motion, namely, the motion of moving the legs of the person to be assisted P or the like having weakened legs.

Figure 10:
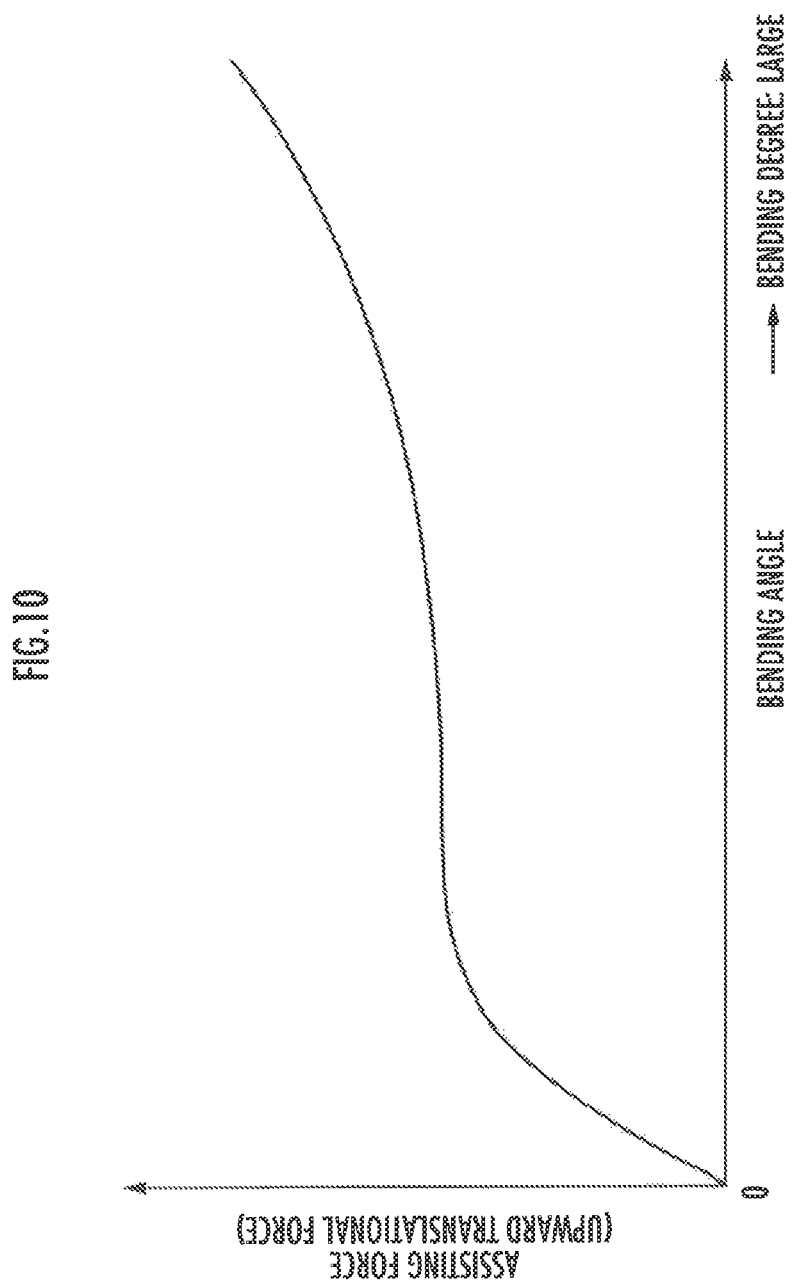
FIG. 10 is a graph illustrating an example of the change characteristics of an assisting force generated by the motion assisting apparatus in the embodiment.

The motion assisting apparatus 1 according to the present embodiment has, for example, the operation characteristics illustrated by the graph of FIG. 10. The graph of FIG. 10 illustrates an example of the relationship between the assist force acting on the person to be assisted P by the elastic force of the elastic structure 31 imparted to each of the knee joint mechanisms 5 (i.e. the translational force acting upward with respect to the upper body) and the degree of bending (i.e. the bending angle) between the thigh frame 2 and the crus frame 3.

In this example, the upward translational force from the elastic force of the elastic structure 31 increases with high sensitivity as the degree of bending (the bending degree) between the thigh frame 2 and the crus frame 3 increases in the range in which the degree of bending is relatively small, i.e. the range in which the leg link mechanism 7 is almost fully extended. Further, when the bending degree increases to a certain level, the upward translational force from the elastic force of the elastic structure 31 increases relatively gradually as the bending degree increases.

The operation characteristics of the motion assisting apparatus 1 are not limited to the characteristics illustrated in FIG. 10, and a variety of operation characteristics can be implemented by, for example, the selection of the elastic characteristic of the elastic member 41 of each of the elastic structures 31 or the setting of the shape of the outer peripheral portion of the first link 21 (the portion engaging with the wire 32) in each of the knee joint mechanisms 5.

The motion assisting apparatus 1 according to the present embodiment configured as described above is capable of providing the following advantages.

The elastic member 41 of each of the elastic structures 31 is constructed to have many hermetically sealed air chambers, as in, for example, a closed-cell (closed-pore) rubber sponge. This allows the elastic structures 31 to be lightweight.

Further, each of the elastic members 41 generates, in addition to the elastic force generated by the material thereof, an elastic force generated by the compression (i.e. the reduction in volume) of the plurality of the air chambers in the elastic member 41 (more specifically, the elastic force generated by an increase in the air pressure in the air chambers caused by a reduction in the volume of the air chambers). This enables the elastic structures 31 to increase the elastic forces with high sensitivity by the compression in the direction of the axial center thereof. Hence, the elastic structures 31 are capable of generating relatively large elastic forces even when they are small-sized.

Further, according to the present embodiment, the elastic structure 31 is formed to have the multilayer structure comprising of a plurality of elastic members 41 and the partition plates 42. Further, the wire 32 to which a tension is imparted is inserted in the through hole 43 of the elastic structure 31. This arrangement prevents the occurrence of an abnormal bending state in which the entire elastic structure 31 is excessively bent or the bending direction differs at each local spot in the stacking direction of the elastic structure 31 when the elastic structure 31 is compressed.

Further, according to the present embodiment, the minimum value of the cross-sectional area of the through hole of each of the partition plates 42 of the elastic structure 31 is smaller than the minimum value of the cross-sectional area of the through hole of each of the elastic members 41. This prevents or suppresses the wire 32 from coming in slide contact with the inner peripheral surface of the through hole of each of the elastic members 41 even if the elastic structure 31 is installed to the thigh frame 2 in a bent state, causing the wire 32 to deviate from the center of the through hole 43 of the elastic structure 31, or if the wire 32 deviates from the center of the through hole 43 when the elastic structure 31 is compressed or is expanded from a compressed state. As a result, it is possible to prevent or suppress the occurrence of the friction between the inner peripheral surface of the through hole of the elastic member 41 and the wire 32.

In addition, the inner peripheral surface of the through hole of the partition plate 42 is curved as described above. Further, inner peripheral surface is formed of a slide material. Hence, even if the wire 32 comes in slide contact with the inner peripheral surface of the through hole of the partition plate 42, the force of the friction between the wire 32 and the partition plate 42 is minimized.

Further, the elastic member 41 and the partition plate 42 that are stacked are fixed to each other at their contact surfaces. Therefore, no friction between the contact surfaces will occur when the elastic structure 31 is compressed or expanded from a compressed state.

This arrangement permits maximized prevention of the elastic energy or the like accumulated by the compression of the elastic structure 31 from being wasted as heat energy attributable to the friction. This in turn permits a reduced energy loss. Further, the elastic energy accumulated at the elastic structure 31 can be efficiently converted into the joint power to be applied to the knee joint mechanism 5.

Further, the portion adjacent to the inner periphery around the through hole in the partition plate 42 is formed to be the thick portion 42a. In addition, the inner peripheral surface of the through hole on the inner side of the thick portion 32a is curved as described above. Hence, even if the wire 32 comes in contact with the inner peripheral surface of the through hole of the partition plate 42 when the elastic structure 31 is compressed or is expanded from the compressed state, the contact pressure is dispersed in the direction of the length of the through hole of the partition plate 42. This prevents the pressure of contact between the wire 32 and the partition plate 42 from being concentrated on a local spot of the wire 32 or the partition plate 42. As a result, the occurrence of breakage, damage or the like of the wire 32 can be prevented, thus permitting enhanced durability of the wire 32 and the like.

Further, according to the present embodiment, the base frame of each of the thigh frames 2 is comprising of the first element frame 12, which extends from the base 11 disposed on one side of the waist of the person to be assisted P to the outer side of a knee along the outer side of the thigh of the person to be assisted IP, and the second element frame 13, which extends from the base 11 obliquely on the front side of the thigh to the inner side of the knee.

Therefore, no frame exists on the inner sides of places adjacent to the bases of the legs of the person to be assisted P. This makes it possible to prevent the thigh frame 2 of the leg link mechanism 7 for the right leg of the person to be assisted P and the thigh frame 2 of the leg link mechanism 7 for the left leg from interfering with each other on the inner sides of the thighs of the both legs.

Further, the first element frame 12 of the thigh frame 2 extends substantially in the vertical direction, and the second element frame 13 extends obliquely downward from the base 11. This allows the thigh frame 2 to exhibit relatively high bending stiffness in the pitch direction. This makes it possible to effectively apply, to the person to be assisted P, the force for pushing up the upper body of the person to be assisted P through the intermediary of the body support member 14 when the person to be assisted P bends his or her leg.

Further, the first element frame 12 and the second element frame 13 of the thigh frame 2 can be bent relatively easily to change the interval between their lower portions. This arrangement allows the thigh frame 2 to fit a wide range of thickness of thighs. In addition, maximized prevention of the person to be assisted P from feeling restrained can be achieved.

Further, the second element frame 13 of the thigh frame 2 extends obliquely downward from the outer side to the inner side of a thigh on the front side of the thigh. In addition, the second element frame 13 smoothly curves.

This arrangement enables the person to be assisted P to easily grasp each portion of the second element frame 13 from the upper end thereof to the lower end thereof while taking a natural posture of his or her arm or the like when, for example, the person to be assisted P is sitting on a chair or the like. The arrangement also enables the person to be assisted P to effortlessly exert a force on the second element frame 13 while grasping a portion of the second element frame 13. This enables the person to be assisted P to easily attach or detach the leg link mechanism 7.

Further, the body support member 14 of the thigh frame 2 extends obliquely, on the back side of the thigh, from the base 11 to the lower end portion of the second element frame 13. This arrangement makes it possible to support the thigh from the back side by the body support member 14 from the place on the bottom side to the place on the top side of the thigh when a leg (a support leg) of the person to be assisted P is being bent, i.e. when the elastic force is being applied by the elastic structure 31 to the knee joint mechanism 5.

In particular, the base 11 is a portion disposed at a level that is higher than the inner root of a leg of the person to be assisted P. Therefore, not only the thigh of the person to be assisted P but also a portion in the vicinity of a hip joint or a portion in the vicinity of the ischium can be supported by the body support member 14 extending from the base 11.

Thus, the translational force in the direction for pushing up the upper body of the person to be assisted P can be effectively applied to the person to be assisted P while preventing the translational force from being concentrated on any local spot of the person to be assisted P.

Further, the base 11, which is the upper end portion of the thigh frame 2, is disposed at the level that is higher than the root on the inner side of a leg of the person to be assisted P and disposed at a level that is lower than the hipbone of the person to be assisted P. This makes it possible to prevent the upper end portion of the thigh frame 2 from being pressed against the buttocks of the person to be assisted P when the person to be assisted P turns his or her leg outward or to prevent the upper end portion of the thigh frame 2 from coming in contact with the side face of the upper body of the person to be assisted P when the person to be assisted P bends his or her upper body sideways.

Further, according to the present embodiment, the joint power generating device 8 imparts the elastic force generated by the elastic structure 31 to the knee joint mechanism 5 through the intermediary of the first link 21 of the knee joint mechanism 5. In this case, each of the knee joint mechanisms 5 is configured as described above, so that the rotational displacement amount of the first link 21 can be controlled to be relatively small even when the person to be assisted P bends his or her stretched legs to a maximum degree, as seen from FIG. 4.

Hence, the required expansion and contraction amount of each of the elastic structures 31 can be controlled to a relatively small amount. This means a smaller required space for disposing each of the elastic structures 31, thus permitting a higher degree of freedom of the disposition of the elastic structures 31 and a reduced size of the motion assisting apparatus 1.

Further, the total value of the bending angles of the tubes 55 (more specifically, the value obtained by integrating the curvature of each of the tubes 55 in the direction of the length of the tube 55 over the full length of the tube 55) is smaller. Hence, the friction between the wire 32 and the tube 55 can be reduced.

[Modifications]

The present invention is not limited to the embodiment described above, and may adopt a variety of modes. The following will describe some modifications.

In the embodiment described above, the elastic members 41 of the elastic structures 31, which have been illustrated, have the cylindrical shape. Alternatively, however, the elastic members 41 of the elastic structures 31 are not limited to the cylindrical shape and may adopt a variety of shapes. For example, each of the elastic members 41 may have an external shape, the cross-section of which orthogonal to the stacking direction of the elastic structure 31 (or the external shape of the elastic member 41 as observed in the stacking direction) is elliptical or polygonal.

The elastic member 41 may alternatively adopt a shape in which the external width in the direction orthogonal to the stacking direction of the elastic structure 31 changes in the stacking direction. For example, the elastic member 41 may adopt a change in which the external width of which continuously changes in a concave form (i.e. a form in which the external width becomes minimum at a middle of the elastic member 41) from one end toward the other end of the elastic member 41 in the stacking direction.

Figure 11:
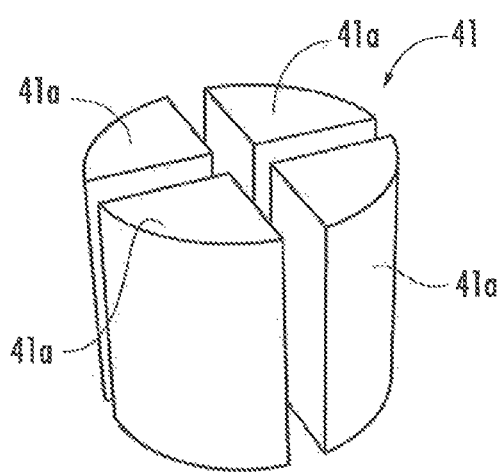
FIG. 11 is a perspective view illustrating another example of the elastic member provided in the elastic structure.

Further, the elastic member 41 of each layer of the elastic structure 31 does not have to have the single unit structure. For example, the elastic member 41 of each layer may be configured in the form of the assembly of a plurality of (four in the illustrated example) element elastic members 41a, which are separated from each other, as illustrated in FIG. 11. In the elastic member 41 illustrated in FIG. 11, the through hole of the elastic member 41, which forms a part of the through hole 43 of the elastic structure 31, is the gap surrounded by all the plurality of the element elastic members 41a constituting the elastic member 41.

Further, the through hole of the elastic member 41 may be formed such that the cross-sectional area thereof changes in the stacking direction of the elastic structure 31.

Further, the elastic member 41 may be configured in a bag shape so as to have a single air chamber.

Further, all of the plurality of the elastic members 41 included in the elastic structure 31 do not have to have the same shape and size. Similarly, all of the plurality of the partition plates 42 included in the elastic structure 31 do not have to have the same shape and size.

Figure 12:
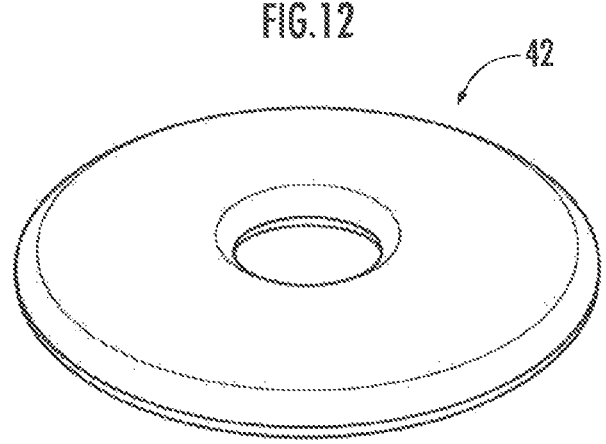
FIG. 12 is a perspective view illustrating another example of the partition plate provided in the elastic structure.

Further, each of the partition plates 42 may be configured, for example, to have a substantially constant thickness (i.e. not to have any thicker portions), as illustrated in FIG. 12.

Figure 13A:
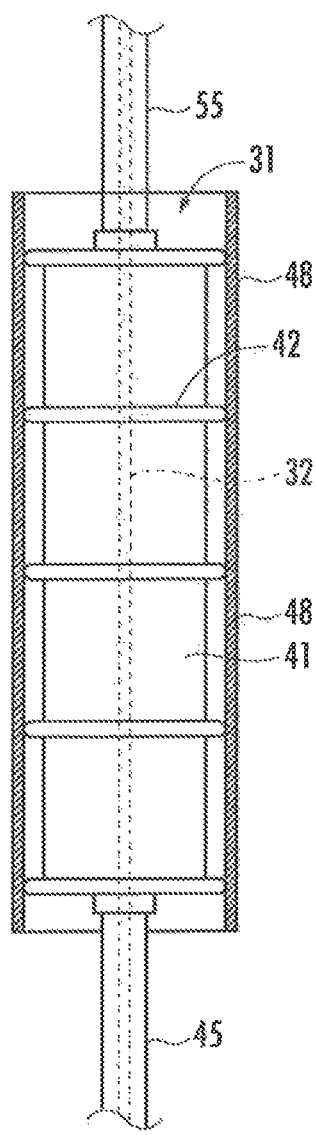
FIG. 13A and FIG. 13B are diagrams illustrating an embodiment which a guide tube is externally inserted onto the elastic structure.
Figure 13B:
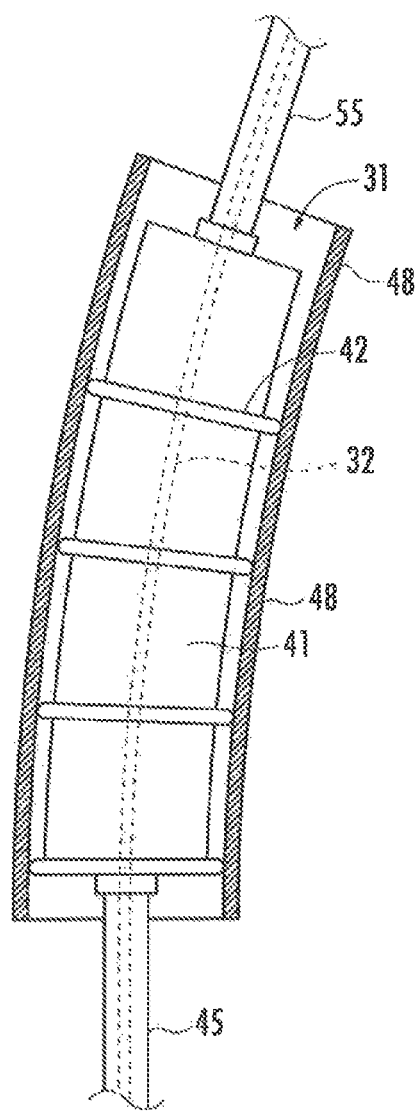

Further, for example, a guide tube 48 extending in the stacking direction of the elastic structure 31 may be externally inserted onto the elastic structure 31 to cause the elastic structure 31 to compress along the inner peripheral surface of the guide tube 48, as illustrated in FIG. 13A or FIG. 13B.

In this case, the compression of the elastic structure 31 will be restricted in the stacking direction of the elastic structure 31 (i.e. the direction of the axial center of the guide tube 48). This makes it possible to reliably prevent the occurrence of the abnormal bending state in which the entire elastic structure 31 excessively bends or the bending direction differs at each local spot in the stacking direction of the elastic structure 31 when the elastic structure 31 is compressed.

If the guide tube 48 is to be installed to the thigh frame 2 together with the elastic structure 31, then the guide tube 48 will be fixed or locked to the thigh frame 2 (i.e. the first element frame 12 or the second element frame 13). Alternatively, the guide tube 48 may be formed integrally with the thigh frame 2.

Further, if the guide tube 48 is externally inserted onto the elastic structure 31 as described above, then the maximum value of the cross-sectional area of each of the partition plates 42 of the elastic structure 31 (i.e. the cross-sectional area in the direction orthogonal to the stacking direction of the elastic structure 31) is preferably set to be larger than the maximum value of the cross-sectional area of the elastic member 41 and set to allow the outer periphery of the partition plate 42 to be in slide contact with the inner peripheral surface of the guide tube 48, as illustrated in FIG. 13A.

This arrangement prevents the elastic member 41 from coming in slide contact with the inner peripheral surface of the guide tube 48 when the elastic structure 31 is compressed. This makes it possible to prevent the friction between the elastic member 41 and the guide tube 48.

The outer peripheral surface of the partition plate 42 or the inner peripheral surface of the guide tube 48 may be formed of a sliding material in order to reduce the coefficient of the friction between the partition plate 42 and the guide tube 48.

Further, the guide tube 48 may be installed such that the elastic structure 31 is curved along the contour of the installation place (the first element frame 12 or the second element frame 13), as illustrated in FIG. 13B. Alternatively, the guide tube 48 may be configured to be deformable in a curve.

This arrangement permits a higher degree of freedom of the installation place of the elastic structure 31 including the guide tube 48. Further, the space required for the installation can be minimized.

Further, as illustrated in FIG. 14, a stretchable net 49 may be provided to cover the outer periphery of the elastic structure 31. A stretchable cylindrical cover may be used in place of the net 49. The net 49 (or the cover) may be made of a material having a small frictional coefficient, such as, for example, a fluororesin.

This arrangement prevents the elastic members 41 of the elastic structure 31 from directly coming in slide contact with the wall surface of the first element frame 12 or the second element frame 13, in which the elastic structure 31 is mounted, when the elastic structure 31 expands or contracts. Further, the elastic members 41 come in slide contact with the wall surface through the intermediary of the net 49 (or the cover). Hence, the friction that may take place between the elastic structure 31 and the wall surface around the elastic structure 31 can be reduced.

With the net 49 (or the cover) attached to the outer periphery of the elastic structure 31 as described above, the guide tube 48 illustrated in FIG. 13A or FIG. 13B may be externally inserted onto the elastic structure 31. In this case, the elastic members 41 can be prevented from directly coming in slide contact with the inner peripheral surface of the guide tube 48 even if the maximum value of the cross-sectional area of each of the partition plates 42 of the elastic structure 31 is approximately the same as the maximum value of the cross-sectional area of the elastic member 41.

Further, in the embodiment described above, the elastic member 41 and the partition plate 42 that are adjacently stacked in the elastic structure 31 are firmly fixed. Alternatively, however, the elastic member 41 and the partition plate 42 that are adjacently stacked may be configured to be in slide contact with each other rather than being firmly fixed.

This arrangement permits enhanced attenuation performance of the vibration of the elastic structure 31 by utilizing the friction that takes place between the elastic member 41 and the partition plate 42 when the elastic structure 31 expands from a compressed state, i.e. when the elastic structure 31 releases the accumulated elastic energy.

Further, the embodiment described above has used the wire 32 as the flexible lengthy member. Alternatively, however, the flexible lengthy member may be belt-shaped or chain-shaped.

Further, the tension imparting mechanism 33 is not limited to the construction described above, and may adopt a variety of forms. For example, a tension imparting mechanism 81 having the construction illustrated in FIG. 15 may be adopted as the tension imparting mechanism.

In the tension imparting mechanism 81, the mechanism for maintaining a constant distance between a middle portion of the disposition path of the other-end-side led out portion of the wire 32 from the elastic structure 31 and the second end of the elastic structure 31 along the disposition path is the same as the tension imparting mechanism 33 in the embodiment described above. More specifically, the mechanism includes a thin long tube 45 disposed between a partition plate 42 at the lower end of each of the elastic structures 31 and a partition wall 15a at the upper end of a joint connection 15.

Meanwhile, the tension imparting mechanism 81 has a lock member 82 fixed to the end of one-end-side led out portion of the wire 32 as a constituent element of the mechanism that binds the one-end-side led out portion to the upper end, i.e. one end, of the elastic structure 31 so as to maintain the length of the one-end-side led out portion of the wire 32 from the elastic structure 31 to be constant. The lock member 82 is brought in contact with or fixed to the opening end peripheral portion of the through hole of the partition plate 42 at the upper end of the elastic structure 31.

Thus, the one-end-side led out portion of the wire 32 is bound to the upper end of the elastic structure 31 thereby to maintain the length of the one-end-side led out portion of the wire 32 to be constant (substantially zero in this example) in a state in which a tension is being imparted to the wire 32 by pulling the other-end-side led out portion of the wire 32 from the elastic structure 31.

Instead of using the lock member 82, a configuration may be adopted, in which the one-end-side led out portion of the wire 32 is fixed to the partition plate 42 at the upper end, i.e. the one end, of the elastic structure 31 through an appropriate fastening member or an adhesive agent or the like.

The tension imparting mechanism 81 further includes moving pulleys 83, each of which is installed to the joint connection 15 of the thigh frame 2, bearings 84 which rotatably support the moving pulleys 83 about the axes of rotation thereof, and an actuator device 54 for controlling the first links 21 of the knee joint mechanisms 5 and the running operations of the wires 32 as the constituent elements of a mechanism that transmits the relative displacement motion, i.e. the bending or stretching motion, of the crus frame 3 with respect to the thigh frame 2 to the other-end-side led out portion of the wire 32 from the elastic structure 31 such that the other-end-side led out portion moves with respect to the lower end, i.e. the other end, of the elastic structure 31 according to the relative displacement motion. The actuator device 54 is the same as the one provided in the tension imparting mechanism 33 of the foregoing embodiment.

Each of the moving pulleys 83 is housed in the joint connection 15 such that the moving pulley 83 is translationally movable together with the bearing 84, which supports the moving pulley 83, in the directions toward or away from the first link 21 of the knee joint mechanism 5 (the directions indicated by arrows Y1 and Y2 of FIG. 15).

The directions in which the moving pulleys 83 and the bearings 84 can be moved are restricted by, for example, the inner wall surfaces of the joint connections 15 in which the moving pulleys 83 and the bearings 84 are accommodated.

Further, the bearing 84 for the moving pulley 83 is connected to the first link 21 of the knee joint mechanism 5 through a wire 85, which is an example of the lengthy member, such that the bearing 84 is displaced according to the relative displacement motion, i.e. the bending or stretching motion, of the crus frame 3 with respect to the thigh frame 2.

In this case, one end of the wire 85 on the first link 21 side is fixed to the outer peripheral portion of the first link 21 functioning as the outer peripheral portion of a pulley. Further, the other end of the wire 85 is locked or fixed to the bearing 84.

With this arrangement, the first link 21 of each of the knee joint mechanisms 5 rotates about the axial center of the joint shaft 21a with respect to the thigh frame 2 according to the relative displacement motion of the crus frame 3 with respect to the thigh frame 2 (i.e. the bending or stretching motion of the leg link mechanism 7). As a result, the amount of winding of the wire 85 at the first link 21 increases or decreases.

Thus, on the outer side and the inner side, the moving pulleys 83 and the bearings 84 translationally move toward or away from the first links 21 of the knee joint mechanisms 5 according to the relative displacement motions of the crus frames 3 with respect to the thigh frames 2. In this case, according to the present embodiment, the amount of winding of the wire 85 at each of the first links 21 increases as the bending degree of each of the crus frames 3 with respect to each of the thigh frames 2 increases. This causes each of the moving pulleys 83 to translationally move toward the first link 21.

The other-end-side led out portion of the wire 32 introduced into the joint connection 15 through the tube 45 from each of the elastic structures 31 is wrapped on the outer periphery of the moving pulley 83 accommodated in the joint connection 15 (i.e. the outer periphery of the knee joint mechanism 5 adjacent to the first link 21), as illustrated in FIG. 15.

Further, the other-end-side led out portion of the wire 32 wrapped on the outer periphery of the moving pulley 83 in the outer joint connection 15 is passed through a hole formed in a partition wall 15a of the outer joint connection 15 via the outer periphery of the moving pulley 83 and led into the upper portion of the outer joint connection 15 of the first element frame 12.

Similarly, the other-end-side led out portion of the wire 32 wrapped on the outer periphery of the moving pulley 83 in the inner joint connection 15 is passed through a hole formed in a partition wall 15a of the inner joint connection 15 via the outer periphery of the moving pulley 83 and led into the upper portion of the inner joint connection 15 of the second element frame 13.

Further, the other-end-side led out portion of the wire 32 of the first element frame 12 and the other-end-side led out portion of the wire 32 of the second element frame 13 are passed through a tube 86 of the first element frame 12 and through a tube 86 of the second element frame 13, respectively to a chassis 61 of the actuator device 54. Further, these other-end-side led out portions of the wires 32 are led into the chassis 61 through the holes formed in the chassis 61. Further, the wires 32 are connected to the outer peripheral portions of the pulleys 62 in the chassis 61.

In this case, the tube 86 of the first element frame 12 extends from the outer joint connection 15 in the direction in which the first element frame 12 extends and reaches the base 11. The tube 86 is disposed to further extend from the base 11 and pass through the space outside the thigh frame 2 to reach the chassis 61.

Further, the tube 86 of the second element frame 13 is disposed to extend from the inner joint connection 15 in the direction in which the second element frame 13 extends and to reach the base 11. The tube 86 is disposed to further extend form the base 11 and pass through the space outside the thigh frame 2 to reach the chassis 61.

Further, as with the tubes 55 of the tension imparting mechanism 33 in the embodiment described above, the tubes 86 are configured to exhibit relatively low stiffness against a bending load and exhibit relatively high stiffness against a compression load in the direction of the length of the tubes 86 (i.e. exhibit resistance to expansion and contraction).

The tension imparting mechanism 81 illustrated in FIG. 15 is configured as described above. As with the case of the foregoing embodiment, in the tension imparting mechanism 81, a control unit 67 controls the operation of an electric motor 66 of the actuator device 54 according to the detection signals of a rotation sensor 71 and a ground contact sensor 72.

In this case, when the output torque of the electric motor 66 is being controlled to impart a small torque that permits the prevention of a slack in the wire 32 (e.g. a torque of a predetermined value), if the bending or stretching motion of the leg link mechanism 7 of the knee joint mechanism 5 is carried out, then the moving pulleys 83 in the joint connections 15 rotate to be displaced (i.e. translationally move) according to the bending or stretching motion. Then, as the moving pulleys 83 are displaced, the pulleys 62 (refer to FIG. 7) of the actuator device 54 rotate, and a part of the other-end-side led out portion of the wire 32 from the outer elastic structure 31 that is on the chassis 61 side from the outer periphery of the outer moving pulley 83 and a part of the other-end-side led out portion of the wire 32 from the inner elastic structure 31 that is on the chassis 61 side from the outer periphery of the inner moving pulley 83 move with respect to the first element frame 12 and the second element frame 13, respectively.

In this situation, a compression load does not substantially act on the elastic structures 31. Therefore, the elastic forces of the elastic structures 31 do not substantially act on the knee joint mechanisms 5.

Thus, the person to be assisted P can move the leg in the free leg phase in the same manner as a normal motion as if the leg link mechanism 7 were not attached to the leg.

Meanwhile, in the state in which the output torque of the electric motor 66 is controlled to hold the rotational angles of the pulleys 62 at a constant angle (i.e. to hold the pulleys 62 in a non-rotation state), the moving pulleys 83 are displaced, i.e. translationally moved, toward the first links 21 of the knee joint mechanisms 5 corresponding thereto as the bending degrees of the crus frames 3 with respect to the thigh frames 2 are increased.

Further, at this time, as the moving pulleys 83 are displaced, the other-end-side led out portions of the wires 32 from the elastic structures 31 are pulled. This causes the compression load from the wires 32 to be applied to the upper ends of the elastic structures 31, thus compressing the elastic structures 31. At the same time, the output torque of the electric motor 66 is controlled to increase the tension imparted to the wires 32 to a level that balances the elastic force generated by the compression of the elastic structures 31.

Thus, as with the case of the foregoing embodiment, the elastic force of each of the elastic structures 31 is imparted, as the joint power in the direction for stretching the leg link mechanism 7, to the knee joint mechanism 5 corresponding to the elastic structure 31.

Further, in this case, the resultant force of the elastic force of each of the elastic structures 31 and the tension imparted to the wire 32 (the resultant force being approximately double the elastic force) is imparted to the knee joint mechanism 5 through the intermediary of the bearing 84 of the moving pulley 83 and the wire 85.

Even in the case where the tension imparting mechanism 81 is configured as illustrated in FIG. 15, a modification similar to the modifications described with reference to FIG. 11, FIG. 12, and FIG. 13A and FIG. 13B or FIG. 14 can be adopted.

Further, the tension imparting mechanism 81 may be configured using, for example, a differential mechanism in place of the moving pulleys 83.

Further, the actuator device 54 is not limited to that in the foregoing embodiment. For example, the actuator device 54 may be provided with a brake unit, which is capable of switching between a mode for braking or locking the pulleys 62 to be unrotatable and a mode for releasing the braking or locking state, in place of the electric motor 66. Further, a clutch mechanism capable of cutting off the power transmission between the electric motor 66 and the pulleys 62 may be interposed therebetween. In addition, a pretension mechanism which imparts a low tension to the wires 32 may be provided separately from the electric motor 66 or the brake unit in order to prevent the wires 32 from slacking.

Further, the leg link mechanisms 7 of the motion assisting apparatus 1 are not limited to the constructions described above. For example, the knee joint mechanism of each of the leg link mechanisms 7 may be comprising of a single-axis joint mechanism having a degree of freedom of rotation about one axis in, for example, the direction of the pitch axis.

Further, for example, the thigh frame 2, the crus frame 3 and the foot frame 4 may have constructions that are different from those in the foregoing embodiments.

Further, each of the leg link mechanism 7 may be configured, for example, to have the knee joint mechanism only on one of the outer side and the inner side of the knee.

Further, for example, the leg link mechanism may be configured such that the ankle joint mechanism 6 and the foot frame 4 of the leg link mechanism 7 are omitted and the lower end portion of the crus frame 3 is bound through a belt or the like to the ankle of a leg.

Further, the ankle joint mechanism 6 may be comprising of, for example, a free joint or the like.

Further, the base 11 of the thigh frame 2 may be disposed on the outer side of an upper portion of the thigh.

Further, the leg link mechanisms may adopt, for example, the construction illustrated in FIG. 16 and FIG. 17.

In this example, a leg link mechanism 7A for each leg of the person to be assisted P differs from that in the foregoing embodiments only in the construction of a thigh frame 120. In this case, the thigh frame 120 has a base 121, which is disposed at an upper level of each leg, and more specifically, at a place on the front of the waist of the person to be assisted P that is adjacent to the side surface (namely, a place located approximately at 45 degrees with respect to the longitudinal direction and the lateral direction), and a first element frame 122 and a second element frame 123, which are bifurcated and extended downward from the base 121.

The first element frame 122 extends obliquely downward from the base 121 toward the outer knee joint mechanism 5 on the front side of the thigh of on a leg of the person to be assisted P. Further, the lower end portion of the first element frame 122 (corresponding to the joint connection 15) is connected to the outer knee joint mechanism 5.

Further, the second element frame 123 extends obliquely downward from the base 121 toward the inner knee joint mechanism 5 on the front side of the thigh of the leg of the person to be assisted P. Further, the lower end portion of the second element frame 123 (corresponding to the joint connection 15) is connected to the inner knee joint mechanism 5.

Further, the thigh frame 120 has a body support member 124 disposed on the rear side of the thigh of the leg of the person to be assisted P. The body support member 124 is extended between the base 11 and the lower end portion of the second element frame 123 such that the body support member 124 extends from the base 11 to the lower end portion of the second element frame 123 via the back of the buttock of the person to be assisted P.

The construction of the leg link mechanism 7A illustrated in FIG. 16 and FIG. 17 is the same as that of the leg link mechanism 7 in the foregoing embodiments except for the aspect described above.

The thigh frame 120 in the leg link mechanism 7A configured as described above also exhibits high bending stiffness in the pitch direction. Further, an assisting force in the direction for pushing up the upper body of the person to be assisted P can be properly applied to the person to be assisted P through the intermediary of the body support member 124 by imparting the joint power to the knee joint mechanisms 5 in the same manner as that in the foregoing embodiments.

As described above, the base 121 is disposed at a place located in the direction of approximately 45 degrees with respect to the longitudinal direction and the lateral direction of the person to be assisted P. This prevents the base 121 from coming in contact with the abdomen of the person to be assisted P when the person to be assisted P squats or the like.

Further, in the embodiments or the modifications described above, the motion assisting apparatus 1 adapted to assist the motion of a leg of the person to be assisted P (human being) has been illustrated. However, the elastic force generating device in accordance with the present invention can be also configured to assist the bending and stretching of the arms or the upper body of the person to be assisted P by the elastic forces of elastic structures 31.

Figure 18:
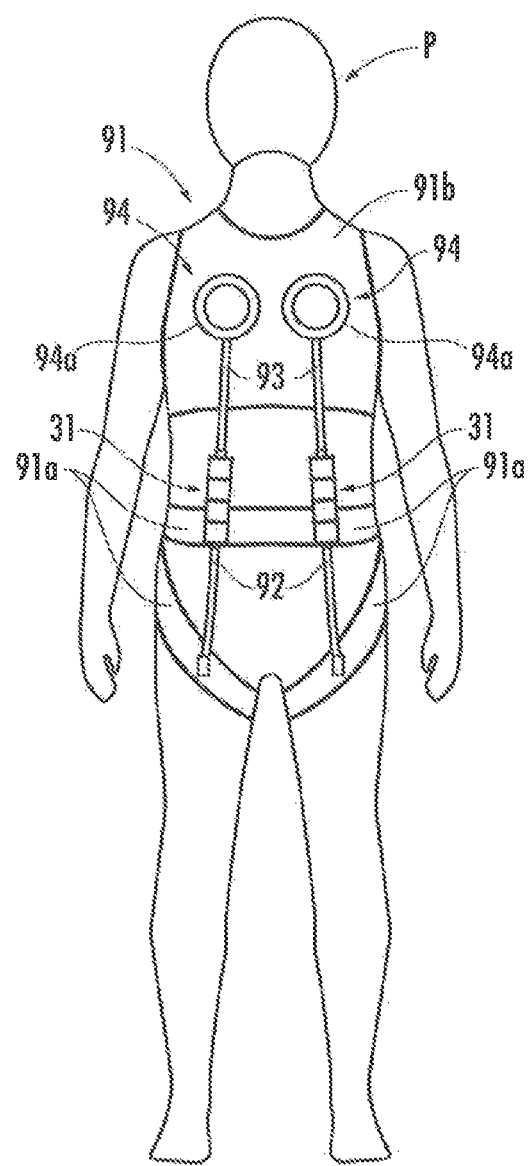
FIG. 18 is a diagram illustrating an example of how the elastic structures are attached in the case where the elastic forces of the elastic structures are applied to the upper body of a person to be assisted.

For example, a motion assisting apparatus 91 configured as illustrated in FIG. 18 is capable of generating an assisting force in a direction for stretching the upper body by the elastic structures 31 when the upper body of the person to be assisted P bends forward. In this example, the motion assisting apparatus 91 has hip-worn parts 91a to be attached to the hip of the person to be assisted P and an upper-body-worn part 91b to be attached to the upper part of the upper body of the person to be assisted P. Further, on the back of the person to be assisted P, the two elastic structures 31, 31 are disposed to be laterally arranged between the hip-worn parts 91a and the upper-body-worn part 91b.

Each of the elastic structures 31 has two wires (flexible lengthy members) 92 and 93 inserted therein. One of the wires, namely, the wire 92, has one end (namely, the upper end) thereof locked or fixed to the upper end of the elastic structure 31. Further, the other end (lower end) of the wire 92 is led out downward from the lower end of the elastic structure 31. Further, the other end (namely, the lower end) of the wire 92 led out from the elastic structure 31 is connected to the hip-worn part 91a.

Further, the other wire 93 has one end (namely, the lower end) thereof locked or fixed to the lower end of the elastic structure 31. Further, the other end (upper end) of the wire 93 is led out upward from the upper end of the elastic structure 31. Further, the other end (namely, the upper end) of the wire 93 led out from the elastic structure 31 is introduced into a chassis of an actuator device 94 installed to the upper-body-worn part 91b. Further, the other end of the wire 93 is fixed by being wrapped on the outer peripheral portion of a pulley (not illustrated) rotatively driven by an electric motor 94a in the chassis.

In the motion assisting apparatus 91 configured as described above, when the upper body of the person to be assisted P is bent forward in a state in which the wires 93 on the upper side are locked to be immovable by the electric motor 94a of the actuator device 94, the elastic structures 31 are compressed, causing the elastic structures 31 to generate an elastic force. The elastic force will act on the upper body of the person to be assisted P as the assisting force for stretching the upper body.

In a state in which a relatively small output torque that makes it possible to remove slack from the wires 92 and 93 is being generated by the electric motor 94a, the length of the portion of each of the wires 93 led out of the elastic structure 31 changes as the upper body bends or stretches. Thus, the elastic structure 31 is substantially not compressed. This makes it possible to prevent the elastic force, which provides the force in the stretching direction, from being generated in the upper body when, for example, the person to be assisted P sits on a chair.

Figure 19:
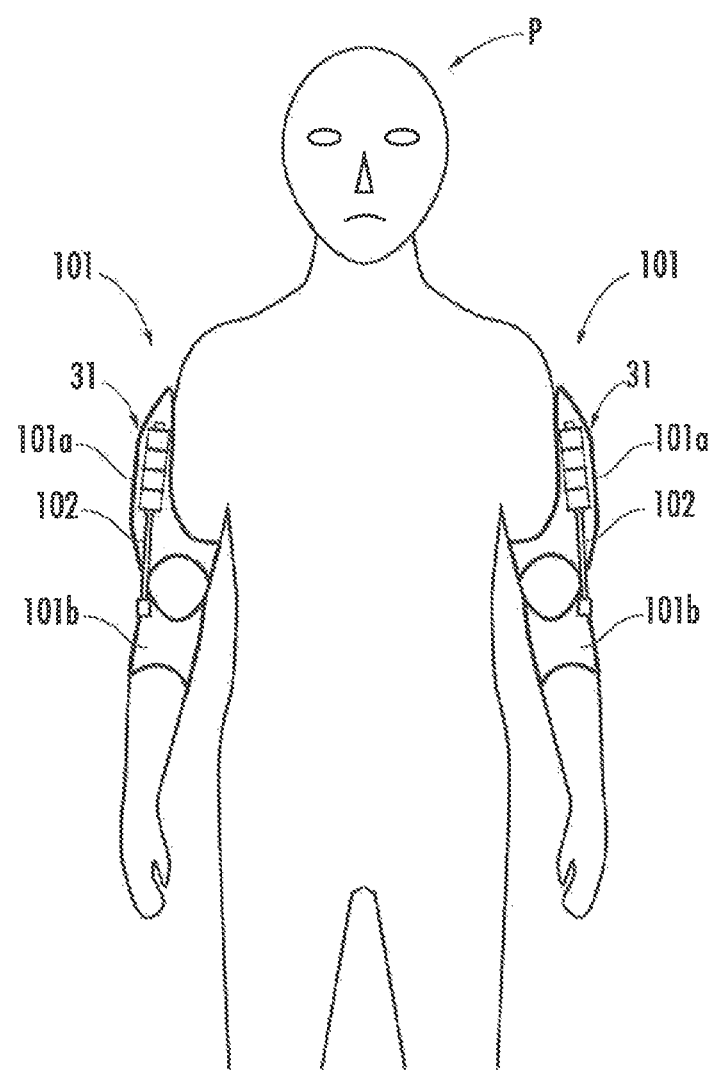
FIG. 19 is a diagram illustrating an example of how the elastic structures are attached in the case where the elastic forces of the elastic structures are applied to the elbows of the arms of a person to be assisted.

Further, a motion assisting apparatus 101 configured as illustrated in, for example, FIG. 19 is capable of generating, by elastic structures 31, an assisting force in the direction for bending the elbow of each arm of the person to be assisted P. In this example, the motion assisting apparatus 101 has an upper-arm-worn part 101a and a forearm-worn part 101b to be attached to the upper arm and the forearm, respectively, of each arm. An elastic structure 31 is mounted on the upper-arm-worn part 101a. In this case, the lower end of the elastic structure 31 is locked or fixed to the upper-arm-worn part 101a.

Further, a wire 102 is inserted in each of the elastic structures 31. One end (namely, the upper end) of the wire 102 is locked or fixed to the upper end of the elastic structure 31. The wire 102 is led out downward from the lower end of the elastic structure 31. Further, the other end (namely, the lower end) of the wire 102 led out from the elastic structure 31 is connected to the forearm-worn part 101b.

In the motion assisting apparatus 101 configured as described above, the elastic structures 31 are compressed when the arms are stretched, causing the elastic structures 31 to generate an elastic force. The elastic force will act on the arms as the assisting force in the direction for bending the elbows of the arms. Hence, the motion of bending the elbows of the arms can be assisted when, for example, the elbows of the arms are bent to lift a relatively heavy object.

Further, a motion assisting apparatus 11I configured as illustrated in, for example, FIG. 20A and FIG. 20B is capable of generating, by elastic structures 31, an assisting force in the direction for raising each arm of the person to be assisted P. In this example, the motion assisting apparatus 111 has an upper-body-worn part 111a to be attached to the upper portion of the upper body of the person to be assisted P and upper-arm-worn parts 111b, 111b to be attached to the upper arms of the arms. Further, the two elastic structures 31, 31 are disposed to be laterally arranged at an upper level on the back of the person to be assisted P.

Each of the elastic structures 31 has two wires (flexible lengthy members) 112 and 113 inserted therein. One of the wires, namely, the wire 112, has one end thereof locked or fixed to the lower end of the elastic structure 31. Further, the wire 112 is led out upward from the upper end of the elastic structure 31. Further, the other end of the wire 112 led out from the elastic structure 31 passes the top of the left or the right shoulder of the person to be assisted P, whichever shoulder is on the same side as the elastic structure 31, and is connected to the upper-arm-worn part 111b on the same side (i.e. the left or the right side).

Further, the other wire, namely, the wire 113, has one end thereof locked or fixed to the upper end of the elastic structure 31. The wire 113 is led out downward from the lower end of the elastic structure 31. Further, the other end of the wire 113 led out from the elastic structure 31 is introduced into a chassis of an actuator device 114 installed to the upper-body-worn part 111a. Further, the other end of the wire 113 is fixed by being wrapped on the outer peripheral portion of a pulley (not illustrated) rotatively driven by an electric motor 114a in the chassis.

In the motion assisting apparatus 111 configured as described above, when an arm of the person to be assisted P is moved down (i.e. an upper arm is extended downward) in a state in which the wire 113 is locked to be immovable by the electric motor 114a of the actuator device 114, the elastic structure 31 corresponding to the arm is compressed, causing the elastic structure 31 to generate an elastic force. The elastic force will act on the arm of the person to be assisted P as the assisting force for raising the arm.

In a state in which a relatively small output torque that makes it possible to remove slack from the wires 112 and 113 is being generated by the electric motor 114a, the length of the portion of each of the wires 113 led out of the elastic structure 31 changes according to the motion of the arm (i.e. the motion by a shoulder joint). Thus, the elastic structure 31 is substantially not compressed. In this condition, the elastic force, which provides the force in the direction for raising the arm, will not be generated even when the arm is moved down.

Further, in the embodiments or the modifications described above, the descriptions have been given of the examples in which the elastic force generating device in accordance with the present invention is applied to the motion assisting apparatus for a person. However, the elastic force generating device in accordance with the present invention is not limited to the application to the motion assisting apparatus for a person, but can be applied to a variety of apparatuses. For example, the elastic force generating device in accordance with the present invention may be used to impart joint powers to the joint mechanisms of a robot.

What is claimed is:

1. An elastic force generating device comprising:
    an elastic structure which is comprising of a multilayer construction formed by alternately stacking a plurality of elastic members, each elastic member of the plurality of elastic members incorporates one or more hermetically sealed air chambers, with each hermetically sealed air chamber of the one or more hermetically sealed air chambers having a volume that decreases by compression, and a plurality of partition plates having higher stiffness than that of the elastic members, the elastic structure has through holes extending in a stacking direction and a total length in the stacking direction that is greater than a minimum width of each of the elastic members in a direction orthogonal to the stacking direction;
    a flexible lengthy member inserted in a particular through hole of the through holes of the elastic structure; and
    a tension imparting mechanism which is a mechanism adapted to variably impart a tension to the flexible lengthy member, the tension imparting mechanism is adapted to transmit a force between the flexible lengthy member and the elastic structure such that, at a time of imparting a tension to the flexible lengthy member, a force for compressing the elastic structure in the stacking direction increases as the tension increases.

2. The elastic force generating device according to claim 1,
wherein the particular through hole of the elastic structure has a partition plate portion and an elastic member portion and is configured such that a minimum value of a cross-section area of the partition plate portion is smaller than a minimum value of a cross-section area of the elastic member portion.

3. The elastic force generating device according to claim 1,
wherein a particular partition plate of the plurality of partition plates is formed such that a first portion adjacent to an inner periphery around the particular through hole is thicker than that of a second portion adjacent to an outer periphery of the partition plate, and that the elastic member is stacked on the second portion adjacent to the outer periphery of the partition plate.

4. The elastic force generating device according to claim 1,
wherein an inner peripheral surface of a partition plate portion of the particular through hole in a particular partition plate of the plurality of partition plates is formed in a curve such that a cross-section area of the particular through hole at a middle portion between both ends in a direction of a thickness of the partition plate is smaller than a cross-section area of the particular through hole at both ends in the direction of a thickness of the particular partition plate.

5. The elastic force generating device according to claim 1,
wherein an inner peripheral surface of a partition plate portion of the particular through hole is comprising of a slide material.

6. The elastic force generating device according to claim 1,
wherein the elastic member is firmly fixed to a particular partition plate of the plurality of partition plates along a surface of contact between the elastic member and the particular partition plate.

7. The elastic force generating device according to claim 1,
wherein the elastic member is in slide contact with a particular partition plate of the plurality of partition plates along a surface of contact between the elastic member and the particular partition plate.

8. The elastic force generating device according to claim 1, further comprising a guide tube which is extended in the stacking direction and externally inserted onto the elastic structure,
wherein the elastic structure is disposed inside the guide tube such that the elastic structure is compressed in the stacking direction along an inner peripheral surface of the guide tube.

9. The elastic force generating device according to claim 8,
wherein a maximum value of a cross-section area of a particular partition plate of the plurality of partition plates has a magnitude which allows the particular partition plate to come in slide contact with the inner peripheral surface of the guide tube, and the maximum value is larger than a maximum value of a cross-section area of the elastic member at the time of compression of the elastic structure.

10. The elastic force generating device according to claim 8,
wherein the guide tube is configured to be curvable or curved.

11. The elastic force generating device according to claim 1, further comprising a stretchable net or cover attached to the elastic structure so as to cover an outer peripheral surface of the elastic structure.

12. The elastic force generating device according to claim 1,
wherein the elastic force generating device applies an elastic force, which is generated by a compression of the elastic structure, to a joint mechanism that connects two members, including a first member and a second member, such that these two members are displaced with respect to one another,
one of both ends of the elastic structure in the stacking direction is defined as a first end and the other end thereof is defined as a second end, and a portion of the flexible lengthy member that is led out of the particular through hole of the elastic structure at the first end of the elastic structure is defined as a first lead-out portion and a portion led out of the particular through hole of the elastic structure at the second end of the elastic structure is defined as a second lead-out portion, and
the tension imparting mechanism is configured to include: a mechanism which binds the first lead-out portion of the flexible lengthy member to the first end of the elastic structure thereby to maintain a constant length of the first lead-out portion; a mechanism which maintains a constant distance between a middle portion of a disposition path of the second lead-out portion of the flexible lengthy member and the second end of the elastic structure, along the disposition path; and a mechanism which transmits a relative displacement motion of the second member to the second lead-out portion of the flexible lengthy member so as to cause the second lead-out portion to move with respect to the second end of the elastic structure according to the relative displacement motion of the second member with respect to the first member.

13. The elastic force generating device according to claim 12,
wherein the tension imparting mechanism is disposed, as an element that transmits a force between the flexible lengthy member and the elastic structure, to extend from the first end of the elastic structure and has a tube in which the first lead-out portion of the flexible lengthy member is inserted, and the tube is configured to be flexible while maintaining a length thereof constant.

14. The elastic force generating device according to claim 12,
wherein the elastic force generating device is adapted to apply the elastic force generated by the compression of the elastic structure to a portion to be assisted, which is a leg, an arm or an upper body of a person, as an assisting force for assisting bending and stretching of the portion to be assisted, and the first member and the second member are adapted to be attached to the portion to be assisted such that the first member and the second member are displaced with respect to one another as the portion to be assisted bends or stretches.

15. The elastic force generating device according to claim 14,
wherein the first member and the second member are comprising of a thigh frame and a crus frame, which are adapted to be attached to the person such that the thigh frame and the crus frame move integrally with a thigh and a crus, respectively, of the leg of a person as the thigh and the crus bend or stretch, and the mechanism that transmits the relative displacement motion of the second member to the second lead-out portion is configured such that the second lead-out portion of the flexible lengthy member moves in a direction for being drawn out of the particular through hole of the elastic structure as a degree of bending between the thigh and the crus of the leg increases.

* * * * *